(12) United States Patent
Gudas et al.

(10) Patent No.: US 11,207,277 B2
(45) Date of Patent: *Dec. 28, 2021

(54) METHODS OF TREATING DISEASES ASSOCIATED WITH HIGH-FAT DIET AND VITAMIN A DEFICIENCY USING RETINOIC ACID RECEPTOR AGONISTS

(71) Applicant: Cornell University, Ithaca, NY (US)

(72) Inventors: Lorraine J Gudas, New York, NY (US); Yannick Benoit, Ontario (CA); Ronald Perez, Somerset, NJ (US); Xiao-Han Tang, Staten Island, NY (US); Steven Trasino, Brooklyn, NY (US)

(73) Assignee: CORNELL UNIVERISITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,780

(22) Filed: Nov. 8, 2019

(65) Prior Publication Data

US 2020/0078318 A1   Mar. 12, 2020

Related U.S. Application Data

(63) Continuation of application No. 16/000,003, filed on Jun. 5, 2018, now Pat. No. 10,525,019, which is a continuation of application No. 15/414,128, filed on Jan. 24, 2017, now Pat. No. 10,010,512, which is a continuation of application No. 14/761,341, filed as application No. PCT/US2014/012083 on Jan. 17, 2014, now Pat. No. 9,585,857.

(60) Provisional application No. 61/754,438, filed on Jan. 18, 2013.

(51) Int. Cl.
*A61K 31/07* (2006.01)
*A61K 31/203* (2006.01)
*A61K 31/192* (2006.01)
*A61K 31/426* (2006.01)

(52) U.S. Cl.
CPC ............ *A61K 31/07* (2013.01); *A61K 31/192* (2013.01); *A61K 31/203* (2013.01); *A61K 31/426* (2013.01)

(58) Field of Classification Search
CPC ...................................................... A61K 31/07
USPC ......................................................... 514/369
See application file for complete search history.

(56) References Cited

U.S. PATENT DOCUMENTS

2006/0189798 A1   8/2006   Blaudin de The et al.
2009/0137671 A1   5/2009   Noy
2012/0316242 A1   12/2012  Noy

FOREIGN PATENT DOCUMENTS

| AU | 27232 95 A | 2/1996 |
| CA | 2802414 A1 | 12/2011 |
| EP | 0 698 392 A1 | 2/1996 |
| WO | WO 97/10819 A1 | 3/1997 |
| WO | WO 99/29330 A1 | 6/1999 |
| WO | WO 02/080935 A1 | 10/2002 |
| WO | WO 2007/009083 A2 | 1/2007 |
| WO | WO 2012/125724 A1 | 9/2012 |
| WO | WO 2012/162698 A1 | 11/2012 |
| WO | WO 2012/175698 A1 | 12/2012 |
| WO | WO 2012/178108 A1 | 12/2012 |

OTHER PUBLICATIONS

Office Action for Corresponding European Application No. 14740346.3 dated Oct. 21, 2020.
N. Idres et al.: "Activation of Retinoic Acid Receptor-Dependent Transcription By All-Trans-Retinoic Acid Receptor-Dependent Transcription By All-Trans-Retioic Acid Metabolites and Isomers" Journal of Biological Chemistry vol. 277, No. 35, Aug. 23, 2002, pp. 31491-31498.
International Search Report dated May 22, 2014.
Chertow et at. "Effects of Vitamin A Deficiency and Repletion on Rat insulin Secretion In Vivo and In Vitro from Isolated Islets," The Journal of Clinical Investigation, Jan. 1, 1987 (Jan. 1, 1987), vol. 79, pp. 163-169. entire document.
Zobali et al. "Effects of vitamin A and insulin on the antioxidative state of diabetic rat heart: a 14 comparison study with combination treatment," Cell Biochemistry and Function, Jun. 1, 2002 (Jun. 1, 2002), vol. 20, pp. 75-80.
Ahmad et al. "Naturally Occurring Antioxidant Vitamin Levels in Patients with Type-II Diabetes 51 Mellitus," J Ayub Med Coli Abbottabad, Jan. 1, 2003 (Jan. 1, 2003), vol. 15, No. 1:54-7, (pp. 1-5).
Ford et al. "The Metabolic Syndrome and Antioxidant Concentrations: Findings from the Third 52 National Health and Nutrition Examination Survey," Diabetes, Sep. 1, 2003 (Sep. 1, 2003), vol. 52, pp. 2346-235.
European Search Report dated Aug. 30, 2016.
Brun PJ, Yang KJ, Lee SA, Yuen JJ, Blaner WS. Retinoids: Potent regulators of metabolism. Biofactors. 2013 2):151-63.
Eun-Jung Rhee et al.: "Retinoid Metabolism 1-14 and Diabetes Mellitus", Diabetes & Metabolism Journal, vol. 36, No. 3, Jan. 1, 2012 (Jan. 1, 2012), p. 16.
Albrechtson E et al: "The Expression of Retinoic Acid Receptors And The Effects In Vitro By Reinoids In Human Pancreatic Cancer Cell Lines", Pancreas, Raven Press, New York, Ny, Us, vol. 25, No. I, Jul. 1, 2002 (Jul. 1, 2002), pp. 49-56.

(Continued)

*Primary Examiner* — Taofiq A Solola
(74) *Attorney, Agent, or Firm* — Mark S. Cohen; Pearl Cohen Zedek Latzer Baratz LLP

(57) ABSTRACT

This invention relates to pharmaceutical composition and methods of using vitamin A and/or RARβ agonist for the treatment or prevention of diseases or conditions associated with high fat diet and/or vitamin deficiency.

16 Claims, 13 Drawing Sheets

Specification includes a Sequence Listing.

(56) References Cited

OTHER PUBLICATIONS

Chertow B S et al: "Effects of Vitamin A Deficiency and Repletion On Rat Glucagon Secretion" Pancreas, Raven Press, New York, Ny, Us vol. 1. 9, No. 4, Jul. 1, 1994 (Jul. 1, 1994), pp. 475-484.
Guariguata L, Whiting D, Weil C, Unwin N. The International Diabetes Federation diabetes atlas methodology for estimating global and national prevalence of diabetes in adults. Diabetes research and clinical practice Dec. 2011 94(3):322-32.
Whiting DR, Guariguata L, Weil C, Shaw J. IDF diabetes atlas: global estimates of the prevalence of diabetes for 2011 and 2030. Diabetes research and clinical practice. [Research Support, Non-U. S. Gov't], Dec. 2011;94(3):311-21.
Huang ES, Basu A, O'Grady M, Capretta JC. Projecting the future diabetes population size and related costs for the U.S. Diabetes Care. [Research Support, N.I.H., Extramural Research Support, Non-U.S. Gov't]. Dec. 2009;32(12):2225-9.
Oliver-Krasinski JM, Staffers DA. On the origin of the beta cell. Genes & development. [Research Support, N.I.H., Extramural Review], Aug. 1, 2008;22(15):1998-2021.
Waldron-Lynch F, Herold KC. Immunomodulatory therapy to preserve pancreatic beta-cell function in type 1 diabetes. Nature reviews Drug discovery. [Review]. Jun. 2011;10(6):439-52.
Waldron-Lynch F, von Herrath M, Herold KC. Towards a curative therapy in type 1 diabetes: remission of autoimmunity, maintenance and augmentation of beta cell mass. Novartis Foundation symposium2008;292:146-55; discussion 55-8, 202-3.
Charbonnel B, Penfornis A, Varroud-Vial M, Kusnik-Joinville O, Detournay B. Insulin therapy for diabetes mellitus: Treatment regimens and associated costs. Diabetes & metabolism Dec. 13, 2011.
Soria B, Andreu E, Berná G, Fuentes E, Gil A, León-Quinto T, Martín F, Montanya E, Nadal A, Reig JA, Ripoll C, Roche E, Sanchez-Andrés JV, Segura J. Engineering pancreatic islets. Pflugers Archiv—European Journal of Physiology2000;440(1):1-18.
Zaret KS, Grompe M. Generation and regeneration of cells of the liver and pancreas. Science. [Research Support, N.I.H., Extramural Research Support, Non-U.S. Gov't Review]. Dec. 5, 2008;322(5907):1490-4.
Weir GC, Cavelti-Weder C, Bonner-Weir S. Stem cell approaches for diabetes: towards beta cell replacement. Genome medicine2011;3(9):61.
Sui J, Mehta M, Shi B, Morahan G, Jiang FX. Directed Differentiation of Embryonic Stem Cells Allows Exploration of Novel Transcription Factor Genes for Pancreas Development. Stem cell reviewJan. 26, 2012;1(1):1-10.
Ben-Yehudah A, White C, Navara CS, Castro CA, Ize-Ludlow D, Shaffer B, Sukhwani M, Mathews CE, Chaillet JR, Witchel SF. Evaluating protocols for embryonic stem cell differentiation into insulinsecreting beta-cells using insulin II-GFP as a specific and noninvasive reporter. Cloning Stem CellsJun. 2009;11(2):245-57.
Blyszczuk P, Czyz J, Kania G, Wagner M, Roll U, St-Onge L, Wobus AM. Expression of Pax4 in embryonic stem cells promotes differentiation of nestin-positive progenitor and insulin-producing cells. Proc Natl Acad Sci USA. [Research Support, Non-U.S. Gov't]. Feb. 4, 2003;100(3):998-1003.
Borowiak M, Maehr R, Chen S, Chen AE, Tang W, Fox JL, Schreiber SL, Melton DA. Small molecules efficiently direct endodermal differentiation of mouse and human embryonic stem cells. Cell Stem Cell Apr. 3, 2009;4(4):348-58.
Jaramillo M, Banerjee I. Endothelial cell co-culture mediates maturation of human embryonic stem cell to pancreatic insulin producing cells in a directed differentiation approach. J Vis Exp2012(61).
Chen Y, Pan FC, Brandes N, Afelik S, Solter M, Pieler T. Retinoic acid signaling is essential for pancreas development and promotes endocrine at the expense of exocrine cell differentiation in Xenopus. Developmental biology. [Comparative Study Research Support, Non-U.S. Gov't]. Jul. 1, 2004;271(1):144-60.
Ostrom M, Loffler KA, Edfalk S, Selander L, Dahl U, Ricordi C, Jeon J, Correa-Medina M, Diez J, Edlund H. Retinoic acid promotes the generation of pancreatic endocrine progenitor cells and their further differentiation into beta-cells. PLoS One. [Research Support, Non-U.S. Gov't]. 2008;3(7):e2841.
Matthews KA, Rhoten WB, Driscoll HK, Chertow BS. Vitamin A deficiency impairs fetal islet development and causes subsequent glucose intolerance in adult rats. The Journal of nutrition. [Research Support, U.S. Gov't, P.H.S.]. Aug. 2004;134(8):1958-63.
Chertow et at. "Effects of Vitamin A Deficiency and Repletion on Rat insulin Secretion In Vivo and In Vitro from Isolated Islets," The Journal of Clinical Investigation, Jan. 1, 1987 (Jan. 1, 1987), vol. 79, pp. 163-169.
Dodge R, Loomans C, Sharma A, Bonner-Weir S. Developmental pathways during in vitro progression of human islet neogenesis. Differentiation. [Research Support, N.I.H., Extramural Research Support, Non-U.S. Gov't]. Feb. 2009;77(2):135-47.
Dolle P, Ruberte E, Leroy P, Morriss-Kay G, Chambon P. Retinoic acid receptors and cellular retinoid binding proteins. I. A systematic study of their differential pattern of transcription during mouse organogenesis. Development. [Research Support, Non-U.S. Gov't]. Dec. 1990;110(4):1133-51.
Ghyselinck NB, Dupe V, Dierich A, Messaddeq N, Garnier JM, Rochette-Egly C, Chambon P, Mark M. Role of the retinoic acid receptor beta (RARβ) during mouse development. The International journal of developmental biology. [Research Support, Non-U.S. Gov't Research Support, U.S. Gov't, P.H.S.]. Jun. 1997;41(3):425-47.
Martinez-Ceballos E, Gudas LJ. Hoxa1 is required for the retinoic acid-induced differentiation of embryonic stem cells into neurons. Journal of neuroscience research. [Research Support, N.I.H., Extramural], Oct. 2008;86(13):2809-19.
Martinez-Ceballos E, Chambon P, Gudas LJ. Differences in gene expression between wild type and Hoxa1 knockout embryonic stem cells after retinoic acid treatment or leukemia inhibitory factor (LIF) removal. The Journal of biological chemistry. [Research Support, N.I.H., Extramural Research Support, U.S. Gov't, P.H.S.]. Apr. 22, 2005;280(16):16484-98.
Benoit YD, Lussier C, Ducharme PA, Sivret S, Schnapp LM, Basora N, Beaulieu JF. Integrin alpha8beta1 regulates adhesion, migration and proliferation of human intestinal crypt cells via a predominant RhoA/ROCK-dependent mechanism. Biology of the cell / under the auspices of the European Cell Biology Organization. [Research Support, Non-U.S. Gov't]. Dec. 2009;101(12):695-708.
Benoit YD, Pare F, Francoeur C, Jean D, Tremblay E, Boudreau F, Escaffit F, Beaulieu JF. Cooperation between HNF-1 alpha, Cdx2, and GATA-4 in initiating an enterocytic differentiation program in a normal human intestinal epithelial progenitor cell line. American journal of physiology Gastrointestinal and liver physiology. [Research Support, Non-U.S. Gov't]. Apr. 2010;298(4):G504-17.
Auclair BA, Benoit YD, Rivard N, Mishina Y, Perreault N. Bone morphogenetic protein signaling is essential for terminal differentiation of the intestinal secretory cell lineage. Gastroenterology Sep. 2007;133(3):887-96.
Yoshino J, Mills KF, Yoon MJ, Imai S. Nicotinamide mononucleotide, a key NAD(+) intermediate, treats the pathophysiology of diet- and age-induced diabetes in mice. Cell MetabOct. 5, 2011;14(4):528-36.
Spokoini R, Kfir-Erenfeld S, Yefenof E, Slonov RV. Glycogen synthase kinase-3 plays a central role in mediating glucocorticoid-induced apoptosis. Mol EndocrinolJun. 2010;24(6):1136-50.
Yamaguchi TP, Takada S, Yoshikawa Y, Wu N, McMahon AP. T (Brachyury) is a direct target of Wnt3a during paraxial mesoderm specification. Genes & developmentDec. 15, 1999;13(24):3185-90.
Otonkoski T, Beattie GM, Maliy Ml, Ricordi C, Hayek A. Nicotinamide is a potent inducer of endocrine differentiation in cultured human fetal pancreatic cells. J Clin InvestSep. 1993;92(3):1459-66.
Lumelsky N, Blondel O, Laeng P, Velasco I, Ravin R, McKay R. Differentiation of embryonic stem cells to insulin-secreting structures similar to pancreatic islets. Science. [Research Support, Non-U.S. Gov't]. May 18, 2001;292(5520):1389-94.
Marchand M, Schroeder IS, Markossian S, Skoudy A, Negre D, Cosset FL, Real P, Kaiser C, Wobus AM, Savatier P. Mouse ES cells over-expressing the transcription factor NeuroDI show increased differentiation towards endocrine lineages and insulin-expressing

(56) References Cited

OTHER PUBLICATIONS cells. The International journal of developmental biology. [Research Support, Non-U.S. Gov't]. 2009;53(4):569-78.
Langton S, Gudas LJ. CYP26A1 knockout embryonic stem cells exhibit reduced differentiation and growth arrest in response to retinoic acid. Developmental biology. [Research Support, N.I.H., Extramural Research Support, U.S. Gov't, Non-P.H.S.]. Mar. 15, 2008;315(2):331-54.
Soria B. In-vitro differentiation of pancreatic beta-cells. DifferentiationOct. 2001;68(4-5):205-19.
Van Hoof D, D'Amour KA, German MS. Derivation of insulin-producing cells from human embryonic stem cells. Stem cell research. [Research Support, Non-U.S. Gov't Review], Sep.-Nov. 2009;3(2-3):73-87.
Bernardo AS, Hay CW, Docherty K. Pancreatic transcription factors and their role in the birth, life and survival of the pancreatic beta cell. Mol Cell EndocrinolNov. 6, 2008;294(1-2):1-9.
Kashyap V, Rezende NC, Scotland KB, Shaffer SM, Persson JL, Gudas LJ, Mongan NP. Regulation of stem cell pluripotency and differentiation involves a mutual regulatory circuit of the NANOG, OCT4, and SOX2 pluripotency transcription factors with polycomb repressive complexes and stem cell microRNAs. Stem cells and developmentSep. 2009;18(7):1093-108.
Rukstalis JM, Habener JF. Neurogenin3: a master regulator of pancreatic islet differentiation and regeneration. IsletsNov.-Dec. 2009;1(3):177-84.
Gosmain Y, Katz LS, Masson MH, Cheyssac C, Poisson C, Philippe J. Pax6 is crucial for beta-cell function, insulin biosynthesis, and glucose-induced insulin secretion. Mol Endocrinol. [Research Support, Non-U.S. Gov't], Apr. 2012;26(4):696-709.
Ahlgren U, Pfaff SL, Jessell TM, Edlund T, Edlund H. Independent requirement for ISL1 in formation of pancreatic mesenchyme and islet cells. Nature. [Research Support, Non-U.S. Gov't]. Jan. 16, 199;385(6613):257-60.
Naujok O, Francini F, Picton S, Bailey CJ, Lenzen S, Jorns A. Changes in gene expression and morphology of mouse embryonic stem cells on differentiation into insulin-producing cells in vitro and in vivo. Diabetes Metab Res RevJul. 2009;25(5):464-76.
Gasa R, Mrejen C, Leachman N, Otten M, Barnes M, Wang J, Chakrabarti S, Mirmira R, German M. Proendocrine genes coordinate the pancreatic islet differentiation program in vitro. Proc Natl Acad Sci U S ASep. 7, 2004;101 (36):13245-50.
Steiner DF, Cunningham D, Spigelman L, Aten B. Insulin biosynthesis: evidence for a precursor. ScienceAug. 11, 1967;157(3789):697-700.
Daly ME, Vale C, Walker M, Littlefield A, Alberti KG, Mathers JC. Acute effects on insulin sensitivity and diurnal metabolic profiles of a high-sucrose compared with a high-starch diet. Am J Clin NutrJun. 1998;67(6):1186-96.
Cryer PE, Axelrod L, Grossman AB, Heller SR, Montori VM, Seaquist ER, Service FJ. Evaluation and management of adult hypoglycemic disorders: an Endocrine Society Clinical Practice Guideline. The Journal of clinical endocrinology and metabolism Mar. 2009;94(3):709-28.
Cai J, Yu C, Liu Y, Chen S, Guo Y, Yong J, Lu W, Ding M, Deng H. Generation of homogeneous PDX1(+) pancreatic progenitors from human ES cell-derived endoderm cells. J Mol Cell Biol. [Research Support, Non-U.S. Gov't]. Feb. 2010;2(1):50-60.
Jonsson J, Carlsson L, Edlund T, Edlund H. Insulin-promoter-factor 1 is required for pancreas development in mice. NatureOct. 13, 1994;371(6498):606-9.
Fujimoto K, Polonsky KS. Pdx1 and other factors that regulate pancreatic beta-cell survival. Diabetes, obesity & metabolismNov. 2009;11 Suppl 4:30-7.

Dalgin G, Ward AB, Hao Ie T, Beattie CE, Nechiporuk A, Prince VE. Zebrafish mnx1 controls cell fate choice in the developing endocrine pancreas. DevelopmentNov. 2011;138(21 ):4597-608.
Vetere A, Marsich E, Di Piazza M, Koncan R, Micali F, Paoletti S. Neurogenin3 triggers beta-cell differentiation of retinoic acid-derived endoderm cells. The Biochemical journalMay 1, 2003;371(Pt 3):831-41.
Dohrmann C, Gruss P, Lemaire L. Pax genes and the differentiation of hormone producing endocrine cells in the pancreas. Meeh DevMar. 15, 2000;92(1):47-54.
American Diabetes A. Diagnosis and classification of diabetes mellitus. Diabetes CareJan. 2005;28 Suppl 1 :S37-42.
Del Prato S, Marchetti P. Beta- and alpha-cell dysfunction in type 2 diabetes. Horm Metab ResNov.-Dec. 2004;36(11-12):775-81.
Riserus U, Willett WC, Hu FB. Dietary fats and prevention of type 2 diabetes. Prog Lipid ResJan. 2009;48(1):44-51.
Sirchia SM, Ren M, Pili R, Sironi E, Somenzi G, Ghidoni R, Toma S, Nicolo G, Sacchi N. Endogenous reactivation of the RARβ2 tumor suppressor gene epigenetically silenced in breast cancer. Cancer researchMay 1, 2002;62(9):2455-61.
Youssef EM, Estecio MR, Issa JP. Methylation and regulation of expression of different retinoic acid receptor beta isoforms in human colon cancer. Cancer Biol TherJan. 2004;3(1):82-6.
House MG, Herman JG, Guo MZ, Hooker CM, Schulick RD, Lillemoe KD, Cameron JL, Hruban RH, Maitra A, Yeo CJ. Aberrant hypermethylation of tumor suppressor genes in pancreatic endocrine neoplasms. Ann SurgSep. 2003;238(3):423-31; discussion 31-2.
Sato N, Fukushima N, Hruban RH, Goggins M. CpG island methylation profile of pancreatic intraepithelial neoplasia. Mod PatholMar. 2008;21(3):238-44.
Volkmar M, Dedeurwaerder S, Cunha DA, Ndlovu MN, Defrance M, Deplus R, Calonne E, Volkmar U, Igoillo-Esteve M, Naamane N, Del Guerra S, Masini M, Bugliani M, Marchetti P, Cnop M, Eizirik DL, Fuks F. DNA methylation profiling identifies epigenetic dysregulation in pancreatic islets from type 2 diabetic patients. EMBO JMar. 21, 2012;31(6):1405-26.
Lund, B. W.; Piu, F.; Gauthier, N. K.; Eeg, A.; Currier, E.; Sherbukhin,V.; Brann, M. R.; Hacksell, U.; Olsson, R. Discovery of a Potent,Orally Available, and Isoform-Selective Retinoic Acid beta2 Receptor Agonist. J. Med. Chem. 2005, 48, 7517-7519.
Vivat-Hannah V et al., Synergistic Cytotoxicity Exhibited by Combination Treatment of Selective Retinoid Ligands with Taxol (Paclitaxel). Cancer Res. 2001,61, 8703-8711.
Millikan LE, Adapalene: an update on newer comparative studies between the various retinoids. Int.J.Dermatol..2000, 39, 784-88.
Chen JY et al. (1995) RAR-specific agonist/antagonists which dissociate transactivation and AP1 transrepression inhibit anchorage-independent cell proliferation. EMBO J. 1995, 14, 1187-97.
Lazo M, Hernaez R, Eberhardt MS, Bonekamp S, Kamel I, Guallar E, Koteish A, Brancati FL, Clark JM.Prevalence of nonalcoholic fatty liver disease in the United States: the Third National Health and Nutrition Examination Survey, 1988-1994. Am J Epidemiol. 2013; 1:38-45.
Loomba R, Sanyal AJ. The global NAFLD epidemic. Nat Rev Gastroenterol Hepatol. 2013; 11:686-90.
Baffy G, Brunt EM, Caldwell SH.Hepatocellular carcinoma in non-alcoholic fatty liver disease: an emerging menace. J Hepatol. 2012;6:1384-91.
Reeves HL, Friedman SL. Activation of hepatic stellate cells—a key issue in liver fibrosis. Front Biosci. 2002;7:808-26.
Puche JE, Saiman Y, Friedman SL. Hepatic stellate cells and liver fibrosis. Compr Physiol. 2013;4):1473-92.
Geerts, A. History, heterogeneity, developmental biology, and functions of quiescent hepatic stellate cells. Semin. Liver Dis. 2001;21:311-335.

A

B

A

B

A

B

C

SEQUENCE LISTING

```
<160> NUMBER OF SEQ ID NOS: 38

<210> SEQ ID NO 1
<211> LENGTH: 22
<212> TYPE: DNA
<213> ORGANISM: Artificial Sequence
<220> FEATURE:
<223> OTHER INFORMATION: mIns1 primer

<400> SEQUENCE: 1
tagtgaccag ctataatcag ag                                            22

<210> SEQ ID NO 2
<211> LENGTH: 20
<212> TYPE: DNA
<213> ORGANISM: Artificial Sequence
<220> FEATURE:
<223> OTHER INFORMATION: mIns1 primer

<400> SEQUENCE: 2
acgccaaggt ctgaaggtcc                                               20

<210> SEQ ID NO 3
<211> LENGTH: 19
<212> TYPE: DNA
<213> ORGANISM: Artificial Sequence
<220> FEATURE:
<223> OTHER INFORMATION: mGcg primer
```

```
<400> SEQUENCE: 3
ccgccgtgcc caagatttt                                                    19

<210> SEQ ID NO 4
<211> LENGTH: 17
<212> TYPE: DNA
<213> ORGANISM: Artificial Sequence
<220> FEATURE:
<223> OTHER INFORMATION: mGcg primer

<400> SEQUENCE: 4
cctgcggccg agttcct                                                      17

<210> SEQ ID NO 5
<211> LENGTH: 20
<212> TYPE: DNA
<213> ORGANISM: Artificial Sequence
<220> FEATURE:
<223> OTHER INFORMATION: mSst* primer

<400> SEQUENCE: 5
gagcccaacc agacagagaa                                                   20

<210> SEQ ID NO 6
<211> LENGTH: 20
<212> TYPE: DNA
<213> ORGANISM: Artificial Sequence
<220> FEATURE:
<223> OTHER INFORMATION: mSst* primer

<400> SEQUENCE: 6
gaagttcttg cagccagctt                                                   20

<210> SEQ ID NO 7
<211> LENGTH: 24
<212> TYPE: DNA
<213> ORGANISM: Artificial Sequence
<220> FEATURE:
<223> OTHER INFORMATION: mNgn3* primer

<400> SEQUENCE: 7
ctgcgcatag cggaccacag cttc                                              24

<210> SEQ ID NO 8
<211> LENGTH: 26
<212> TYPE: DNA
<213> ORGANISM: Artificial Sequence
<220> FEATURE:
<223> OTHER INFORMATION: mNgn3* primer

<400> SEQUENCE: 8
cttcacaaga agtctgagaa caccag                                            26

<210> SEQ ID NO 9
<211> LENGTH: 20
<212> TYPE: DNA
<213> ORGANISM: Artificial Sequence
<220> FEATURE:
<223> OTHER INFORMATION: mRAR  primer

<400> SEQUENCE: 9
gatcctggat ttctacaccg                                                   20

<210> SEQ ID NO 10
<211> LENGTH: 19
```

<212> TYPE: DNA
<213> ORGANISM: Artificial Sequence
<220> FEATURE:
<223> OTHER INFORMATION: mRAR primer

<400> SEQUENCE: 10
cactgacgcc atagtggta                                                    19

<210> SEQ ID NO 11
<211> LENGTH: 23
<212> TYPE: DNA
<213> ORGANISM: Artificial Sequence
<220> FEATURE:
<223> OTHER INFORMATION: mNanog primer

<400> SEQUENCE: 11
aaaggatgaa gtgcaagcgg tgg                                               23

<210> SEQ ID NO 12
<211> LENGTH: 21
<212> TYPE: DNA
<213> ORGANISM: Artificial Sequence
<220> FEATURE:
<223> OTHER INFORMATION: mNanog primer

<400> SEQUENCE: 12
ctggctttgc cctgacttta a                                                 21

<210> SEQ ID NO 13
<211> LENGTH: 24
<212> TYPE: DNA
<213> ORGANISM: Artificial Sequence
<220> FEATURE:
<223> OTHER INFORMATION: mRex1 primer

<400> SEQUENCE: 13
gaaagcagga tcgcctcact gtgc                                              24

<210> SEQ ID NO 14
<211> LENGTH: 23
<212> TYPE: DNA
<213> ORGANISM: Artificial Sequence
<220> FEATURE:
<223> OTHER INFORMATION: mRex1 primer

<400> SEQUENCE: 14
cgataagaca ccacagtaca cac                                               23

<210> SEQ ID NO 15
<211> LENGTH: 24
<212> TYPE: DNA
<213> ORGANISM: Artificial Sequence
<220> FEATURE:
<223> OTHER INFORMATION: mCyp26a1 primer

<400> SEQUENCE: 15
gaaacattgc agatggtgct tcag                                              24

<210> SEQ ID NO 16
<211> LENGTH: 23
<212> TYPE: DNA
<213> ORGANISM: Artificial Sequence
<220> FEATURE:
<223> OTHER INFORMATION: mCyp26a1 primer

<400> SEQUENCE: 16

```
cggctgaagg cctgcataat cac                                           23

<210> SEQ ID NO 17
<211> LENGTH: 23
<212> TYPE: DNA
<213> ORGANISM: Artificial Sequence
<220> FEATURE:
<223> OTHER INFORMATION: mPax-6 primer

<400> SEQUENCE: 17
gcaaccccca gtccccagtc aga                                           23

<210> SEQ ID NO 18
<211> LENGTH: 24
<212> TYPE: DNA
<213> ORGANISM: Artificial Sequence
<220> FEATURE:
<223> OTHER INFORMATION: mPax-6 primer

<400> SEQUENCE: 18
agtccattcc cgggctccag ttca                                          24

<210> SEQ ID NO 19
<211> LENGTH: 18
<212> TYPE: DNA
<213> ORGANISM: Artificial Sequence
<220> FEATURE:
<223> OTHER INFORMATION: mIsl-1* primer

<400> SEQUENCE: 19
cccgggggcc actatttg                                                 18

<210> SEQ ID NO 20
<211> LENGTH: 17
<212> TYPE: DNA
<213> ORGANISM: Artificial Sequence
<220> FEATURE:
<223> OTHER INFORMATION: mIsl-1* primer

<400> SEQUENCE: 20
cgggcacgca tcacgaa                                                  17

<210> SEQ ID NO 21
<211> LENGTH: 20
<212> TYPE: DNA
<213> ORGANISM: Artificial Sequence
<220> FEATURE:
<223> OTHER INFORMATION: mIapp* primer

<400> SEQUENCE: 21
tgggctgtag ttcctgaagc                                               20

<210> SEQ ID NO 22
<211> LENGTH: 20
<212> TYPE: DNA
<213> ORGANISM: Artificial Sequence
<220> FEATURE:
<223> OTHER INFORMATION: mIapp* primer

<400> SEQUENCE: 22
gcacttccgt ttgtccatct                                               20

<210> SEQ ID NO 23
<211> LENGTH: 20
<212> TYPE: DNA
<213> ORGANISM: Artificial Sequence
```

```
<220> FEATURE:
<223> OTHER INFORMATION: HPRT1 primer

<400> SEQUENCE: 23
tgctcgagat gtgatgaagg                                                    20

<210> SEQ ID NO 24
<211> LENGTH: 20
<212> TYPE: DNA
<213> ORGANISM: Artificial Sequence
<220> FEATURE:
<223> OTHER INFORMATION: HPRT1 primer

<400> SEQUENCE: 24
tcccctgttg actggtcatt                                                    20

<210> SEQ ID NO 25
<211> LENGTH: 20
<212> TYPE: DNA
<213> ORGANISM: Artificial Sequence
<220> FEATURE:
<223> OTHER INFORMATION: RAR-beta-2 primer

<400> SEQUENCE: 25
tggcattgtt tgcacgctga                                                    20

<210> SEQ ID NO 26
<211> LENGTH: 22
<212> TYPE: DNA
<213> ORGANISM: Artificial Sequence
<220> FEATURE:
<223> OTHER INFORMATION: RAR-beta-2 primer

<400> SEQUENCE: 26
cccccctttg gcaaagaata ga                                                 22

<210> SEQ ID NO 27
<211> LENGTH: 23
<212> TYPE: DNA
<213> ORGANISM: Artificial Sequence
<220> FEATURE:
<223> OTHER INFORMATION: CYP26A1 RAR-beta-2 primer

<400> SEQUENCE: 27
ctttataagg ccgcccaggt tac                                                23

<210> SEQ ID NO 28
<211> LENGTH: 22
<212> TYPE: DNA
<213> ORGANISM: Artificial Sequence
<220> FEATURE:
<223> OTHER INFORMATION: CYP26A1 RAR-beta-2 primer

<400> SEQUENCE: 28
cccgatccgc aattaaagat ga                                                 22

<210> SEQ ID NO 29
<211> LENGTH: 21
<212> TYPE: DNA
<213> ORGANISM: Artificial Sequence
<220> FEATURE:
<223> OTHER INFORMATION: LRAT primer

<400> SEQUENCE: 29
tctggcatct ctcctacgct g                                                  21
```

```
<210> SEQ ID NO 30
<211> LENGTH: 24
<212> TYPE: DNA
<213> ORGANISM: Artificial Sequence
<220> FEATURE:
<223> OTHER INFORMATION: LRAT primer

<400> SEQUENCE: 30
gttccaagtc cttcagtctc ttgc                                          24

<210> SEQ ID NO 31
<211> LENGTH: 22
<212> TYPE: DNA
<213> ORGANISM: Artificial Sequence
<220> FEATURE:
<223> OTHER INFORMATION: INS2 primer

<400> SEQUENCE: 31
tgtggggagc gtggcttctt ct                                            22

<210> SEQ ID NO 32
<211> LENGTH: 22
<212> TYPE: DNA
<213> ORGANISM: Artificial Sequence
<220> FEATURE:
<223> OTHER INFORMATION: INS2 primer

<400> SEQUENCE: 32
cagctccagt tgtgccactt gt                                            22

<210> SEQ ID NO 33
<211> LENGTH: 19
<212> TYPE: DNA
<213> ORGANISM: Artificial Sequence
<220> FEATURE:
<223> OTHER INFORMATION: HPRT primer

<400> SEQUENCE: 33
tgctcgagtg tgatgaagg                                                19

<210> SEQ ID NO 34
<211> LENGTH: 19
<212> TYPE: DNA
<213> ORGANISM: Artificial Sequence
<220> FEATURE:
<223> OTHER INFORMATION: HPRT primer

<400> SEQUENCE: 34
tccctgttga ctggtcatt                                                19

<210> SEQ ID NO 35
<211> LENGTH: 19
<212> TYPE: DNA
<213> ORGANISM: Artificial Sequence
<220> FEATURE:
<223> OTHER INFORMATION: TNF-alpha primer

<400> SEQUENCE: 35
```

```
cctgtagccc acgtcgtag                                    19

<210> SEQ ID NO 36
<211> LENGTH: 22
<212> TYPE: DNA
<213> ORGANISM: Artificial Sequence
<220> FEATURE:
<223> OTHER INFORMATION: TNF-alpha primer

<400> SEQUENCE: 36
gggagtagac aaggtacaac cc                                22

<210> SEQ ID NO 37
<211> LENGTH: 23
<212> TYPE: DNA
<213> ORGANISM: Artificial Sequence
<220> FEATURE:
<223> OTHER INFORMATION: MCP1 primer

<400> SEQUENCE: 37
ttaaaaacct ggatcggaac caa                               23

<210> SEQ ID NO 38
<211> LENGTH: 23
<212> TYPE: DNA
<213> ORGANISM: Artificial Sequence
<220> FEATURE:
<223> OTHER INFORMATION: MCP1 primer

<400> SEQUENCE: 38
gcattagctt cagatttacg ggt                               23
```

METHODS OF TREATING DISEASES ASSOCIATED WITH HIGH-FAT DIET AND VITAMIN A DEFICIENCY USING RETINOIC ACID RECEPTOR AGONISTS

CROSS-REFERENCE TO RELATED APPLICATIONS

This application is a continuation of U.S. patent application Ser. No. 16/000,003, filed Jun. 5, 2018, which is a continuation of U.S. patent application Ser. No. 15/414,128, filed Jan. 24, 2017, which is a continuation of U.S. patent application Ser. No. 14/761,341 filed Jul. 16, 2015, which is a national phase application of PCT International Application PCT/US2014/012083, filed Jan. 17, 2014, which claims priority to and the benefit of U.S. Provisional Application Ser. No. 61/754,438, filed Jan. 18, 2013, all of which are incorporated herein by reference in its their entirety.

GOVERNMENT FUNDING

This invention was made with Government support under Grant Number R01 CA043796 awarded by National Institutes of Health (NCI) and Grant Number R01 DE10389 from the Dental and Craniofacial Institute. The United States Government has certain rights in the invention.

FIELD

The invention relates to the treatment and prevention of various diseases or conditions caused by fat accumulation or vitamin deficiency.

BACKGROUND

After smoking, high fat diet is said to be the second most lethal habit, causing 300,000 deaths each year in the U.S. alone. High fat diet leads to many health problems, including obesity, stroke, cancer, high blood pressure, diabetes, osteoarthritis, rheumatoid arthritis, multiple sclerosis, heart disease, and diseases in other organs such as liver and kidney.

Diabetes is a group of pancreatic diseases characterized by high blood glucose levels that result from defects in the body's ability to produce and/or use insulin. In 2011 there were an estimated 366 million cases of diabetes worldwide, according to the International Diabetes Federation, and these cases are estimated to increase to 522 million by 2030 (1, 2). In the U.S. there were 23.7 million diagnosed cases, with an estimated healthcare cost of $113 billion (2, 3). Diabetes results when insulin production by pancreatic $\beta$-cells does not meet the metabolic demand of peripheral tissues such as liver, fat, and muscle (4). A reduction in $\beta$-cell number and function leads to hyperglycemia in both type I and type II diabetes (4). In type I diabetes, insulin-producing pancreatic $\beta$-cells lose self-tolerance and this gives rise to hyperglycemia (5). Each year in the United States there are over 30,000 new cases of type I diabetes diagnosed (6). Patients with type I diabetes can control their blood glucose level with insulin supplements (7). However, the differentiation of stem cells into pancreatic $\beta$-cells could be a long term, better solution (8-10).

Type II diabetes is more common. In type II diabetes the body does not use insulin properly, thus it is called insulin resistance. At first, the pancreas may make extra insulin to make up for it. But over time there won't be enough insulin to keep blood glucose at normal levels. Type II diabetes is an increasingly prevalent disease that due to a high frequency of complications leads to a significant reduction of life expectancy. Because of diabetes associated microvascular complications, type II diabetes is currently the most frequent cause of adult-onset loss of vision, renal failure, and amputations in the industrialized world. In addition, the presence of type II diabetes is associated with a two to five fold increase in cardiovascular disease risk. After long duration of disease, most patients with type II diabetes will eventually fail on oral therapy and become insulin dependent with the necessity for daily injections and multiple daily glucose measurements.

A third type of diabetes, gestational diabetes, is developed by many women usually around the 24th week of pregnancy. Treatment for gestational diabetes aims to keep blood glucose levels equal to those of pregnant women who don't have gestational diabetes.

Some patients with diabetes can manage their conditions with healthy eating and exercise. Some will need to have prescribed medications and/or insulin to keep blood glucose levels. In addition, diabetes is a progressive disease. Even if medication is not required at first, it may be needed overtime.

Non-alcoholic fatty liver disease (NAFLD) is marked by lipid accumulation in hepatocytes (steatosis) without evidence of hepatitis or liver fibrosis (69, 70). NAFLD is a major risk factor for development of non-alcohol steatohepatitis (NASH) and hepatocellular carcinoma (71). Driven by rising rates of obesity, diabetes and insulin resistance, NAFLD is currently the most common form of liver disease in the United States with an estimated 55 million cases (69). At the current rate, NAFLD will reach epidemic proportions in the United States by 2030; yet no FDA approved pharmacological therapy exist for prevention or treatment of NAFLD (69).

Over the last decade, experimental animal and human data suggests that hepatic stellate cells (HSCs) are an important cellular target for development of pharmacological therapies for prevention or treatment of NAFLD spectrum liver diseases (73). HSCs are star-like cells that reside in the liver sinusoids whose main function are to store 80-90% of the total body vitamin A (VA) pool (74). During hepatic injury HSCs losing their VA storage capacity, trans-differentiate into myofibroblasts and orchestrate wound healing by secreting components of extra-cellular matrix including type 1 collagen (colla1) and alpha-smooth muscle actin ($\alpha$-SMA) (72, 73). During pathogenesis of unchecked NAFLD, HSCs proliferate and become highly fibrotic through hyper-secretion colla1 and $\alpha$-SMA leading to liver scarring and an inflammation cascade that drives further hepatic fibrosis and liver damage (72,73).

Diabetes is the most common cause of kidney failure, accounting for nearly 44 percent of new cases. Even when diabetes is controlled, the disease can lead to Chronic Kidney Disease (CKD) and kidney failure. Nearly 24 million people in the United States have diabetes, and nearly 180,000 people are living with kidney failure as a result of diabetes. People with kidney failure undergo either dialysis, an artificial blood-cleaning process, or transplantation to receive a healthy kidney from a donor. In 2005, care for patients with kidney failure cost the United States nearly $32 billion.

There is an unmet medical need for methods, medicaments and pharmaceutical compositions with regard to disease-modifying properties and with regard to reduction of high fat diet or vitamin A deficiency associated diseases while at the same time showing a good safety profile.

SUMMARY

This invention discloses pharmaceutical compositions and methods for treating and preventing diseases in pancreas, liver, kidney, testes, as well as other organs that are associated with high fat diet and/or vitamin A deficiency.

According to certain embodiments, the invention provides a method of treating or preventing a pancreatic disease in a subject comprising administering to the subject vitamin A or an agonist of retinoic acid receptor-beta (RARβ).

In certain embodiments, the pancreatic disease is associated with obesity.

In certain embodiments, the pancreatic disease is associated with a high fat diet.

In certain embodiments, the pancreatic disease is associated with vitamin A deficiency in the pancreas.

The pancreatic disease may be diabetes, which may be type I or type II diabetes, or gestational diabetes.

According to certain embodiments, the invention provides a method of increasing RARβ level in a subject comprising administering to the subject vitamin A or an agonist of retinoic acid receptor-beta (RARβ).

In certain embodiments, RARβ level is increased in an organ.

The organ may be pancreas, liver, kidney, or testes.

According to certain embodiments, the invention provides a method of treating or preventing the degeneration of pancreatic beta cells in a subject comprising administering to the subject vitamin A or an agonist of retinoic acid receptor-beta (RARβ).

According to certain embodiments, the invention provides a method of maintaining or improving the function of pancreatic beta cells in a subject comprising administering to the subject vitamin A or an agonist of retinoic acid receptor-beta (RARβ).

According to certain embodiments, the invention provides a method of maintaining or improving pancreatic insulin secretion in a subject comprising administering to the subject vitamin A or an agonist of retinoic acid receptor-beta (RARβ).

According to certain embodiments, the invention provides a method of maintaining or improving insulin sensitivity in a subject comprising administering to the subject vitamin A or an agonist of retinoic acid receptor-beta (RARβ).

According to certain embodiments, the invention provides a method of maintaining or improving the level of glucagon in a subject comprising administering to said subject vitamin A or an agonist of retinoic acid receptor-beta (RARβ).

According to certain embodiments, the invention provides a method of treating or preventing fat deposit of a subject comprising administering to the subject vitamin A or an agonist of retinoic acid receptor-beta (RARβ).

According to certain embodiments, the invention provides a method of treating or preventing inflammation of a subject comprising administering to the subject vitamin A or an agonist of retinoic acid receptor-beta (RARβ).

According to certain embodiments, the invention provides a method of decreasing the level of an inflammatory mediator in a subject comprising administering to the subject vitamin A or an agonist of retinoic acid receptor-beta (RARβ).

According to certain embodiments, the invention provides a method of decreasing oxidative stress in a subject comprising administering to the subject vitamin A or an agonist of retinoic acid receptor-beta (RARβ).

In certain embodiments, the production of the inflammatory mediator is decreased.

In certain embodiments, the secretion of the inflammatory mediator is decreased.

The inflammatory mediator may be monocyte chemotactic protein (mcp-1) or tumor necrosis factor alpha (tnf-α) according to certain embodiments.

In certain embodiments, the fat deposit, inflammation or oxidative stress is in an organ.

The organ may be pancreas, liver, kidney, or testes.

According to certain embodiments, the invention provides a method of treating or preventing a liver disease in a subject comprising administering to the subject vitamin A or an agonist of retinoic acid receptor-beta (RARβ).

In certain embodiments, the liver disease is associated with obesity.

In certain embodiments, the liver disease is associated with a high fat diet.

In certain embodiments, the liver disease is associated with vitamin A deficiency.

In certain embodiments, the liver disease is fatty liver disease (FLD), liver fibrosis, or hepatic steatosis.

In certain embodiments, the liver disease is non-alcoholic FLD (NAFLD), alcohol associated FLD, or non-alcoholic steatohepatitis (NASH).

In certain embodiments, the liver disease is associated with reduced vitamin A level in the liver.

According to certain embodiments, the invention provides a method of decreasing the activation of hepatic stellate cells (HSCs) in a subject comprising administering to the subject vitamin A or an agonist of retinoic acid receptor-beta (RARβ).

According to certain embodiments, the invention provides a method of decreasing the level of hepatic reactive oxygen species (ROS) in a subject comprising administering to the subject vitamin A or an agonist of retinoic acid receptor-beta (RARβ).

According to certain embodiments, the invention provides a method of decreasing the level of alpha smooth muscle actin (α-SMA) in a subject comprising administering to the subject vitamin A or an agonist of retinoic acid receptor-beta (RARβ).

According to certain embodiments, the invention provides a method of increasing the level of lethicin:retinol acyltransferase (LRAT) in the liver of a subject comprising administering to the subject vitamin A or an agonist of retinoic acid receptor-beta (RARβ).

According to certain embodiments, the invention provides a method of increasing the level of RARβ in the liver of a subject comprising administering to the subject vitamin A or an agonist of retinoic acid receptor-beta (RARβ).

According to certain embodiments, the invention provides a method of decreasing the level of SRBP1c in the liver of a subject comprising administering to the subject vitamin A or an agonist of retinoic acid receptor-beta (RARβ).

In certain embodiments, the subject has a liver disease.

In certain embodiments, the liver disease is fatty liver disease (FLD), liver fibrosis, or hepatic steatosis.

In certain embodiments, the liver disease is non-alcoholic FLD (NAFLD), alcohol associated FLD, or non-alcoholic steatohepatitis (NASH).

In certain embodiments, the liver disease is associated with reduced vitamin A level in the liver.

In certain embodiments, the liver disease is associated with a pancreas disease.

According to certain embodiments, the invention provides a method of treating or preventing a kidney disease in a subject comprising administering to the subject vitamin A or an agonist of retinoic acid receptor-beta (RARβ).

In certain embodiments, the kidney disease is associated with obesity.

In certain embodiments, the kidney disease is associated with a high fat diet.

In certain embodiments, the kidney disease is kidney fibrosis.

In certain embodiments, the kidney disease is a chronic kidney disease.

In certain embodiments, the kidney disease is associated with a pancreatic disease.

In certain embodiments, the kidney disease is associated with a liver disease.

In certain embodiments, the kidney disease is associated with reduced vitamin A level in the kidney.

According to certain embodiments, the invention provides a method of increasing the level of lethicin:retinol acyltransferase (LRAT) in the kidney of a subject comprising administering to the subject vitamin A or an agonist of retinoic acid receptor-beta (RARβ).

According to certain embodiments, the invention provides a method of treating or preventing a disease associated with an organ-specific vitamin A deficiency in a subject comprising administering to the subject vitamin A or an agonist of retinoic acid receptor-beta (RARβ).

In certain embodiments, the organ-specific vitamin A deficiency is associated with obesity.

In certain embodiments, the organ-specific vitamin A deficiency is associated with a high fat diet.

In certain embodiments, the subject has a normal serum level of vitamin A or retinyl esters.

The organ may be pancreas, liver, or kidney.

According to certain embodiments, the invention provides a method of treating or preventing fibrosis in a subject comprising administering to the subject an agonist of retinoic acid receptor-beta (RARβ).

According to certain embodiments, the invention provides a method of decreasing the accumulation of fat in a subject comprising administering to the subject an agonist of retinoic acid receptor-beta (RARβ).

In certain embodiments, the fibrosis or accumulation of fat is in an organ.

The organ may pancreas, liver, kidney, or testes.

According to certain embodiments, the vitamin A or agonist of retinoic acid receptor-beta (RARβ) is administered three times daily.

In certain embodiments, the vitamin A or agonist of retinoic acid receptor-beta (RARβ) is administered at an amount from 30-200 mg per day.

In certain embodiments, the vitamin A or agonist is administered at an amount from 50-150 mg per day.

In certain embodiments, the vitamin A or agonist is administered at an amount from 50-100 mg per day/

In certain embodiments, the vitamin A or agonist is administered at an amount from 100-150 mg per day.

In certain embodiments, the vitamin A or agonist of retinoic acid receptor-beta (RARβ) is administered orally.

In certain embodiments, the vitamin A or agonist of retinoic acid receptor-beta (RARβ) is administered intravenously or subcutaneously.

In certain embodiments, the vitamin A or agonist of retinoic acid receptor-beta (RARβ) does not elevate serum triglyceride in the subject.

In certain embodiments, the vitamin A or agonist of retinoic acid receptor-beta (RARβ) does not increase cardiovascular risk in the subject.

In certain embodiments, a therapeutic effective amount of the vitamin A or agonist of RARβ is administered.

In certain embodiments, both vitamin A and an agonist of RARβ are both administered to the subject.

In certain embodiments, vitamin A and an agonist of RARβ are administered concomitantly.

In certain embodiments, vitamin A and an agonist of RARβ are administered sequentially.

According to certain embodiments, the invention provides a pharmaceutical composition comprising vitamin A or an agonist of retinoic acid receptor-beta (RARβ) or a pharmaceutically acceptable salt thereof at an amount from about 10 mg to about 60 mg.

In certain embodiments, the amount of the vitamin A or agonist is from 15 mg to about 50 mg.

In certain embodiments, the amount of the vitamin A or agonist is from 15 mg to about 35 mg.

In certain embodiments, the amount of the vitamin A or agonist is from about 35 mg to about 50 mg.

In certain embodiments, the amount of the vitamin A or agonist is from about 30 mg to about 200 mg.

In certain embodiments, the amount of the vitamin A or agonist is from about 50 mg to about 150 mg.

In certain embodiments, the amount of the vitamin A or agonist is from about 50 mg to about 100 mg.

In certain embodiments, the amount of the vitamin A or agonist is from about 100 mg to about 150 mg.

According to certain embodiments, the invention provides a pharmaceutical composition comprising vitamin A or an agonist of retinoic acid receptor-beta (RARβ) or a pharmaceutically acceptable salt thereof at a concentration from about 0.1 mg to about 10 mg per 100 ml.

In certain embodiments, the concentration is from about 0.5 mg to about 5 mg per 100 ml.

In certain embodiments, the concentration is from about 1 mg to about 2.5 mg per 100 ml.

In certain embodiments, the agonist is a highly specific RARβ agonist.

In certain embodiments, the agonist is AC261066.

In certain embodiments, the agonist is AC55649.

In certain embodiments, the pharmaceutical composition comprises both vitamin A and an agonist of RARβ.

DETAILED DESCRIPTION

Figure 1:
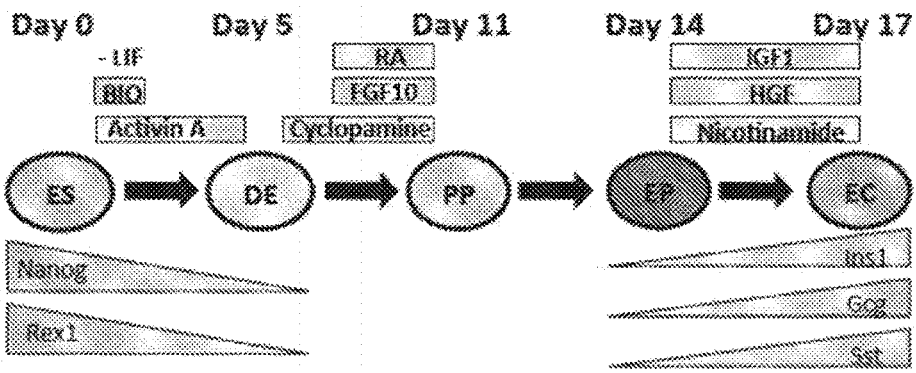
FIG. 1: Pancreatic endocrine differentiation protocol and its impact on the molecular level. (A) Schematic representation of the endocrine differentiation protocol adapted from D'Amour et al. (2006) used on mouse ES cells. Briefly, embryonic stem (ES) cells are treated with different growth factors to successively differentiate into definitive endoderm (DE), pancreatic progenitor (PP), endocrine progenitor (EP), and endocrine cells (EC). (B) WT mouse ES cells were subjected to the 17-day differentiation protocol. Each lane represents a different condition at specific time points. RT-PCR analyses were performed to monitor the expression of pancreatic differentiation markers such as insulin-1 (Ins1), glucagon (Gcg), somatostatin (Sst), neurogenin-3 (Ngn3), Pdx1 and Sox17, as well as the stem cell markers Nanog and Rex1. HPRT1 amplification was used as a control housekeeping gene. Pancreas extracts from C57BL/6 WT mice were used as a positive control.
Figure 1:
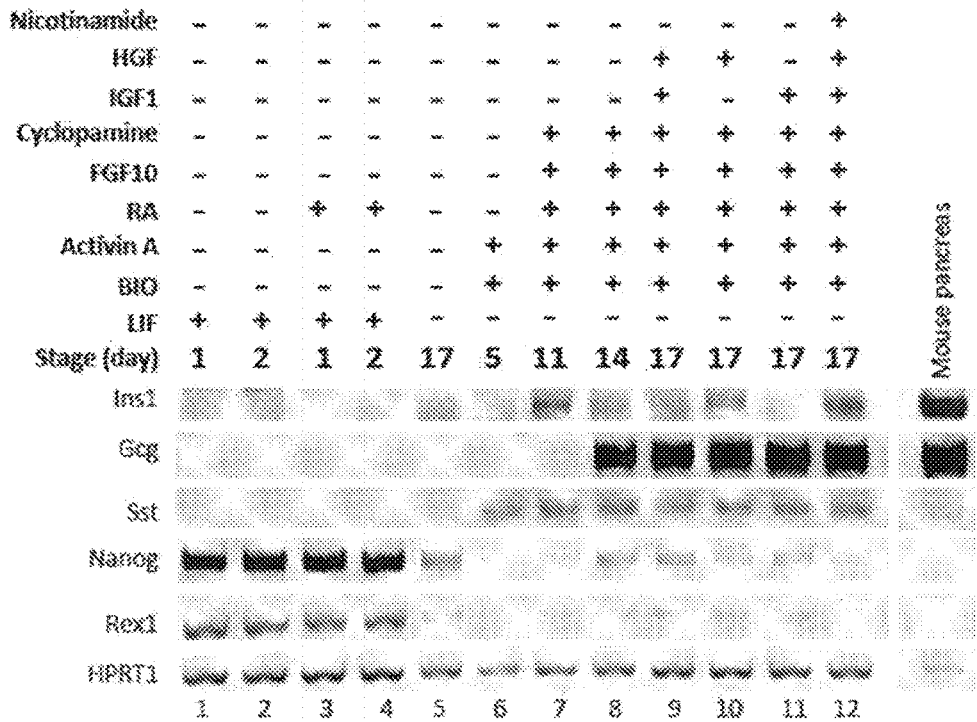

As discussed above, there remains a need to provide alternate therapies or management for a variety of diseases associated with high fat diet and vitamin A deficiency. Accordingly, the present invention relates to uses of vitamin A and retinoic acid receptor β (RARβ) agonists in this regard.

Mouse embryonic stem (ES) cells are pluripotent cells derived from the inner cell mass of blastocyst-stage (day 3.5) embryos (10, 11). Upon LIF removal, ES cells spontaneously differentiate into all three primary embryonic germ layers: endoderm, mesoderm, and ectoderm (10). Several research groups have shown that the directed differentiation of ES cells along the endocrine pathway can be achieved by using a wide range of growth/differentiation factors, including retinoic acid (RA) treatment (12-17).

Although the effects of RA on cells and tissues are known to occur through the activation of retinoic acid receptors (RARα, RARβ, and RARγ) and their isoforms (6, 18), the events occurring downstream of RA signaling that direct the differentiation of definitive endoderm into endocrine precursors are poorly understood (4, 5, 19).

A series of in vivo experiments, including some in Xenopus revealed, however, that RA signaling is crucial for endocrine pancreatic development (20). For instance, mice containing an inducible transgene for the dominant negative RARα403 mutant, used to ablate retinoic acid-dependent processes in vivo, lacked both a dorsal and ventral pancreas, and died at the neonatal stage (21). Impaired pancreatic islet development and repletion were also observed in vivo, in vitamin A deficiency models (22, 23). Moreover, a study of the developmental pathways involved during in vitro islet neogenesis revealed a 3-fold induction of RAR) transcripts from ""adherent"" to ""expanded"" stages of endocrine differentiation (24). Another study, based on the role of CRABP1 and RBP4 in pancreatic differentiation, corroborated the up-regulation of RARβ in early differentiation (11). While previous studies suggested that RARβ is essential to pancreas development, little is known about its functional role in pancreas formation and islet maintenance in adults (25, 26).

Vitamin A metabolite all trans-retinoic acid (RA) acting through its cognate receptors, retinoic acid receptor (RAR) alpha, beta, gamma, possesses anti-obesity and anti-lipogenic properties through regulation of genes involved in energy metabolism and adipogenesis (75).

Using animal models, the present inventors have discovered that retinoic acid receptor β (RARβ) plays an important role in organ development, maintenance, and function. The inventors discovered that vitamin A and RARβ agonists increase RARβ function and signaling; vitamin A and these RARβ agonists also increase the level of RARβ.

The present inventors also discovered that vitamin A and RARβ agonists are effective in treating and preventing high fat diet associated disease in pancreas, liver, kidney, testes and other organs. Furthermore, the inventors discovered that vitamin A and such (RARβ) agonists can restore vitamin A signaling in organs that show vitamin A deficiencies.

Vitamin A and these RARβ agonists, according to the discovery of the present inventors, increase insulin signaling, decrease fat deposit, prevent inflammation, and decrease oxidative stress in various organs, including pancreas, liver, kidney and testes. They also decrease the level of alpha smooth muscle actin (α-SMA) but increase the level of lethicin:retinol acyltransferase (LRAT) and RARβ. When used to treat liver diseases, vitamin A and these RARβ agonists decrease the activation of hepatic stellate cells (HSCs) and the level of hepatic reactive oxygen species (ROS).

The present inventors discovered that vitamin A or agonists of retinoic acid receptor-beta (RARβ) do not elevate serum triglyceride or increase cardiovascular risk at a clinically significant level.

The retinoic acid receptor (RAR) is a type of nuclear receptor that is activated by both all-trans retinoic acid and 9-cis retinoic acid. There are three retinoic acid receptors (RAR), RARα, RARβ, and RARγ, encoded by the RARα, RARβ, RARγ genes, respectively. Each receptor isoform has several splice variants: two—for α, four—for β, and two—for γ.

RAR heterodimerizes with RXR and in the absence of ligand, the RAR/RXR dimer binds to hormone response elements known as retinoic acid response elements (RAREs) complexed with corepressor protein. Binding of agonist ligands to RAR results in dissociation of corepressor and recruitment of coactivator protein that, in turn, promotes transcription of the downstream target gene into mRNA and eventually protein.

Known RARβ agonists include but are not limited to: AC261066, AC55649, LE135, Tazarotene, Adapalene, CD666, 9-cis-retinoic acid, BMS641 and TTNPB. AC261066 and AC55649 are highly-specific RARβ agonists. The term "highly-specific RARβ agonists" also include other agonists having a binding affinity similar to AC261066 or AC55649, e.g., at least 50% or greater, preferably 75% or greater, more preferably 90% or greater of the RARβ binding affinity of AC261066 or AC55649.

RARβ agonists include the fluorinated alkoxythiazoles previously described (65), such as:

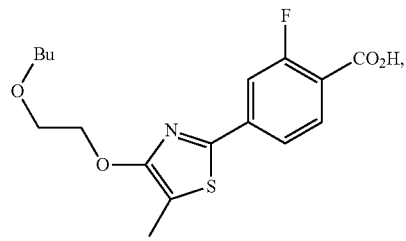

4'-Octyl-[1,1'-biphenyl]-4-carboxylic acid (65), Adapalene (67), BMS-231973, BMS-228987, BMS-276393, BMS-209641 (66), BMS-189453 {4-[(1E)-2-(5,6-Dihydro-5,5-dimethyl-8-phenyl-2-naphthalenyl)ethenyl]-benzoic acid} (68), CD2019 (6-[4-methoxy-3-(1-methylcyclohexyl)phenyl]naphthalene-2-carboxylic acid), compounds described in WO2008/064136 and WO2007009083 and tazarotene (ethyl 6-[2-(4,4-dimethyl-3,4-dihydro-2H-1-benzothiopyran-6-yl)ethynyl]pyridine-3-carboxylate).

AC261066:

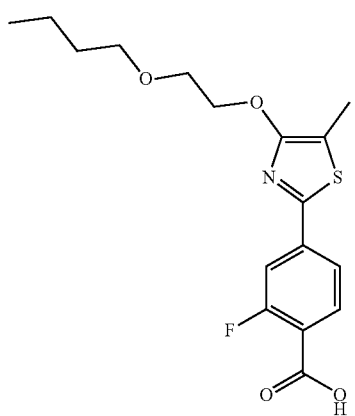

AC55649:

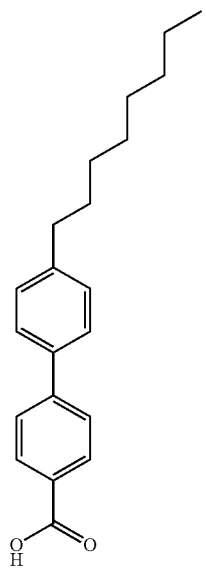

Tazarotene:

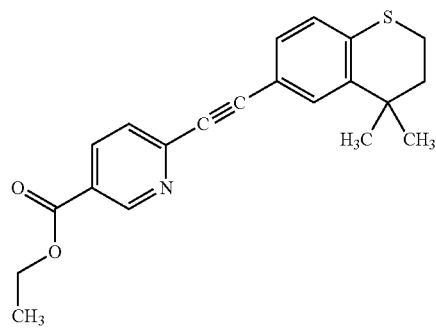

Adapalene:

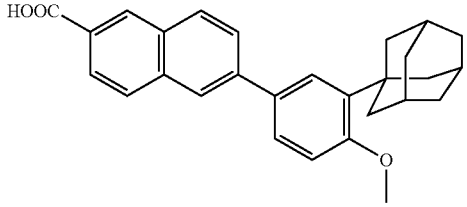

CD666:

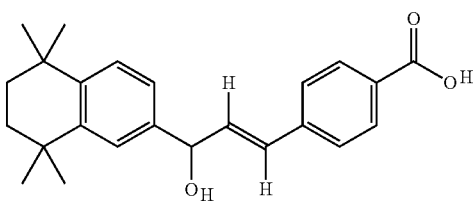

-continued 9-cis-retinoic acid:

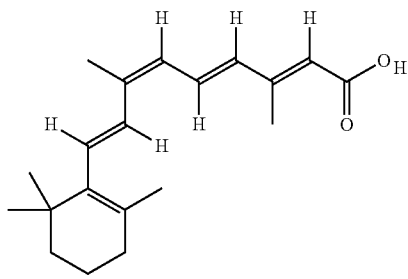

BMS641:

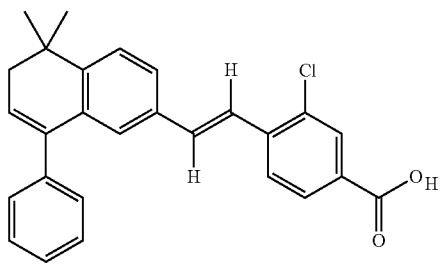

TTNPB:

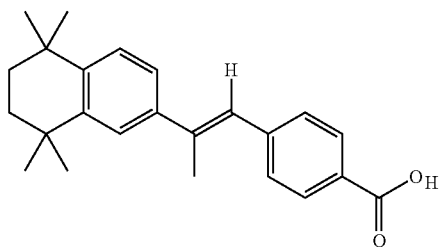

TTNPB:

The highly specific RARβ agonist, e.g., AC261066, can prevent hepatic steatosis and activation of HSCs, marked by decreased expression of α-SMA. AC261066 can significantly diminish hepatic gene expression of pro-inflammatory mediators tumor necrosis factor-alpha (TNFα) and monocyte chemotactic protein-1 (MCP-1).

As used herein, the term "subject" means an animal, preferably a mammal, and most preferably a human. A subject may be a patient having a disease or disorder as discussed herein.

As used herein, the term "vitamin A deficiency" refers to a lack of vitamin A or a decreased level of vitamin in serum or an organ (e.g., pancreas, liver, kidney or testes) of an animal, e.g., human.

As used herein, the terms "decreasing" and "reducing" are used interchangeably to refer to a negative change in the level, activity or function of a molecule, cell or organ. It is meant that the particular level, activity or function is lower by about 25%, about 50%, about 75%, about 90%, about 1-fold, about 2-fold, about 5 fold, about 10-fold, about 25-fold, about 50-fold, or about 100 fold, or lower, when compared to a control.

As used herein, the terms "increasing", "improving" and "enhancing" are used interchangeably to refer to a positive change in the level, activity or function of a molecule, cell or organ. It is meant that the particular level, activity or function is higher by about 25%, about 50%, about 75%, about 90%, about 1-fold, about 2-fold, about 5 fold, about 10-fold, about 25-fold, about 50-fold, or about 100 fold, or higher, when compared to a control.

The expressions "therapeutically effective" and "therapeutic effect" refer to a benefit including, but not limited to, the treatment or amelioration of symptoms of a proliferative disorder discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of vitamin A or an agonist of RARβ is therapeutically effective if it is sufficient to effect the treatment or amelioration of symptoms of a disease discussed herein.

The term "clinically significant level" is used herein to refer to a level of a side effect such as cardiovascular risk caused by the administration of a pharmaceutical composition (e.g., vitamin A or RARβ agonist) that a physician treating the subject would consider to be significant.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 30%, preferably 20%, more preferably 10%.

As used herein, the term "comprises" means "includes, but is not limited to."

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

If a pharmaceutically acceptable salt of vitamin A or agonist of RARβ is utilized in pharmaceutical compositions, the salt preferably is derived from an inorganic or organic acid or base. For reviews of suitable salts, see, e.g., Berge et al, J. Pharm. Sci. 66: 1-19 (1977) wad Remington: The Science and Practice of Pharmacy, 20th Ed., ed. A. Gennaro, Lippincott Williams & Wilkins, 2000.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The term "carrier" is used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., ed. A. Gennaro, Lippincott Williams & Wilkins, 2000 discloses various carriers used in formulating pharmaceutically acceptable compositions and known techniques for the preparation thereof.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

The vitamin A or agonist of RARβ can be administered by any method known to one skilled in the art. For example, vitamin A or agonist of RARβ may be administered orally or parenterally.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Combination therapies that comprise the combination of vitamin A and agonist of RARβ of the present invention, and further with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of vitamin A or agonist of RARβ of the present invention and/or the one or more other therapeutic agents.

The amount or suitable dosage of vitamin A or agonist of RARβ depends upon a number of factors, including the nature of the severity of the condition to be treated, the route of administration and the age, weight, general health, and response of the individual subject. In certain embodiments, the suitable dose level is one that achieves this therapeutic response and also minimizes any side effects associated with the administration. For example, vitamin A or agonist of RARβ may be administered at an amount from about 30 mg to about 200 mg per day, e.g., about 50 mg to about 150 mg per day, about 50 to about 100 mg per day, about 100 mg to about 150 mg per day.

Vitamin A or agonist of RARβ may be administered in single or divided or multiple doses. It will be understood that a suitable dosage of vitamin A or agonist of RARβ may be taken at any time of the day or night, with food or without food. In some embodiments, the treatment period during which an agent is administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

EXAMPLES

The present description is further illustrated by the following examples, which should not be construed as limiting in any way. The contents of all cited references (including literature references, issued patents, published patent appli-

Example 1—Materials and Methods

Cell Culture and Isolation of RARβ Homozygous ES Cell Line.

Mouse J1 wild-type FS cells were cultured as described previously (27). C57BL/6 RARβ heterozygous mice were provided by Dr. Pierre Chambon (Strasbourg-Cedex, France) (26). Homozygous RARβ-null mice were obtained following mating of RARβ heterozygous mice. Blastocysts were harvested on day E3.5 and individually cultured on ES cell medium as previously described (28).

Pancreatic Endocrine Differentiation Protocol.

A slightly modified version of the established protocols published by Borowiak (14) and D'Amour (15) was used to carry out differentiation of hormone expressing endocrine cells from mouse ESCs. Prior to differentiation. ESCs were seeded at $5 \times 10^5$ on 30 mm gelatin-coated plates. After overnight culture, cells were exposed to 250 nM BIO-Acetoxime (EMD Bioscience, San Diego, Calif.)+50 ng/ml activin A (R&D Systems, Minneapolis, Minn.) in Advanced RPMI (GIBCO, Grand Island, N.Y.) supplemented with 1× L-Glu and 0.2% FBS (GIBCO) for 1 day, and then to activin A alone in the same media. Cells were then cultured for 4 days to induce endoderm differentiation. For pancreatic progenitor induction, the cells were transferred to 50 ng/ml FGF10 (R&D Systems), 7.5 μM cyclopamine (Calbiochem, San Diego, Calif.) in DMEM supplemented with 1× L-Glu, 1× Pen/Strep, and 1× B27 (Invitrogen, Grand Island, N.Y.) for 2 days. At day 7, cells were transferred to FGF10, cyclopamine and 2 μM all-trans RA (Sigma, St. Louis, Mo.) in DMEM supplemented with 1× L-Glu, 1× Pen/Strep, and 1× B27 (Invitrogen) for 4 days. At day 11, cells were cultured in the presence of DMEM supplemented with 1× L-Glu, 1× Pen/Strep, and 1× B27 for 3 days. At day 14, CMRL (Invitrogen) medium was added and supplemented with 1× L-Glu, 1× Pen/Strep, 1× B27, 50 ng/ml IGF-1 (R&D Systems), 50 ng/ml HGF (R&D Systems), and 10 mM nicotinamide (Sigma) for 3 more days. All stock compounds were made in either PBS or ethanol.

RT-PCR Analysis.

Various markers for endodermal (day 5), pancreatic progenitor (day 11), endocrine progenitor (day 14) and endocrine (day 17) differentiation were analyzed by semi-quantitative RT-PCR in J1 wild-type and RARβ KO ESCs. Specific primers used and amplification conditions are listed in Table-1. Primers were designed around introns whenever possible. Primers not designed around introns are shown in Table 1 with an asterisk. Total RNA extraction, semi-quantitative and quantitative PCR reactions were performed as previously described (18). Amplified PCR products were resolved on 1.5% agarose gels and visualized by staining with ethidium bromide. PCR bands were sequenced for verification of the correct amplicon. Quantitation of semi-quantitative gels was performed using ImageJ software (National Institutes of Health) from three experimental biological repeats.

TABLE 1

Primer sequences used for RT-PCR

| Primer | Application | Forward sequence (5'→3') | Reverse sequence (5'→3') | Product size (bp) |
|---|---|---|---|---|
| mIns1 | RT-PCR | GTGACCAGCTATAATCAGAG (SEQ ID No. 1) | ACGCCAAGGTCTGAAGGTCC (SEQ ID No. 2) | 289 |
| mGcg | RT-PCR | GCCGTGCCCAAGATTTT (SEQ ID No. 3) | CCTGCGGCCGAGTTCCT (SEQ ID No. 4) | 232 |
| mSst* | RT-PCR | GCCCAACCAGACAGAGAA (SEQ ID No. 5) | GAAGTTCTTGCAGCCAGCTT (SEQ ID No. 6) | 150 |
| mNgn3* | RT-PCR | TGCGCATAGCGGACCACAGCTTC (SEQ ID No. 7) | CACAAGAAGTCTGAGAACACCAG (SEQ ID No. 8) | 233 |
| mRARβ | RT-PCR | GATCCTGGATTTCTACACCG (SEQ ID No. 9) | CTGACGCCATAGTGGTA (SEQ ID No. 10) | 248 |
| mNanog | RT-PCR | AAAGGATGAAGTGCAAGCGGTGG (SEQ ID No. 11) | GGCTTTGCCCTGACTTTAA (SEQ ID No. 12) | 520 |
| mRex1 | RT-PCR | AAAGCAGGATCGCCTCACTGTGC (SEQ ID No. 13) | GATAAGACACCACAGTACACAC (SEQ ID No. 14) | 641 |
| ηCyp26a1 | RT-PCR | GAAACATTGCA-GATGGTGCTTCAG (SEQ ID No. 15) | CGGCTGAAGGCCTGCATAATCAC (SEQ ID No. 16) | 272 |
| mPax-6 | RT-PCR | AACCCCCAGTCCCCAGTCAGA (SEQ ID No. 17) | AGTCCATTCCCGGGCTCCAGTTCA (SEQ ID No. 18) | 399 |
| mIsl-1* | RT-PCR | CGGGGGCCACTATTTG (SEQ ID No. 19) | GGCACGCATCACGAA (SEQ ID No. 20) | 397 |

TABLE 1 -continued

Primer sequences used for RT-PCR

| Primer | Application | Forward sequence (5'→3') | Reverse sequence (5'→3') | Product size (bp) |
|---|---|---|---|---|
| mIapp* | RT-PCR | GGCTGTAGTTCCTGAAGC (SEQ ID No. 21) | ACTTCCGTTTGTCCATCT (SEQ ID No. 22) | 199 |
| HPRT1 | RT-PCR | CTCGAGATGTGATGAAGG (SEQ ID No. 23) | CCCTGTTGACTGGTCATT (SEQ ID No. 24) | 192 |

All primers for RT-PCR are designed around introns, except those marked with *.

Indirect Immunofluorescence.

Immunofluorescence assays on cells and tissue sections were performed as previously described (29). Briefly, differentiated samples were fixed using 4% (w/v) paraformaldehyde and membrane permeabilization (for cells only) was done with 0.3% (w/v) Triton-X 100 (Sigma). Unspecific sites were blocked using 2% BSA for 30 min prior to incubation with rabbit polyclonal anti-PDX1 (Millipore, 06-1379, 1:1000), rabbit anti-C-Peptide (Cell Signaling, 4593, 1:500, Danvers, Mass.) and mouse monoclonal anti-Glucagon (Abcam, ab10988, 1:200) primary antibodies. Phalloidin-TRITC (Millipore, FAK100, 1:1000, Billerica, Mass.) was used to stain the actin stress fiber network (F-actin). Nuclei were stained using DAPI contained in Vectashield® mounting medium for fluorescence (Vector labs, Burlingame, Calif.). Quantitation of C-peptide positive stained cells and islet surface area was performed using MS-Elements Advanced Research software (Nikon).

Western Blot Analysis.

Proteins were extracted from mouse pancreas, separated by SDS-PAGE, and transferred onto nitrocellulose membranes as previously described (30, 31). Membranes were blocked in PBS containing 5% skim milk and 0.1% TWEEN 20 (BioRad, Hercules, Calif.). Rabbit anti-C-Peptide (Cell Signaling, 4593, 1:500), mouse monoclonal anti-Glucagon (Abcam, ab10988, 1:500) and anti-actin (Millipore, MAB1501, 1:2000) primary antibodies were incubated with membranes overnight at 4° C.

Mouse Blood Glucose Assays.

C57BL/6 WT and RAR KO mice were used for this experiment as previously described (26). Briefly, mice were fasted for 15 hours overnight and a 50% dextrose solution (2 g/kg body weight) was injected intraperitoneally. Blood glucose levels were measured from the tail vein at 0, 15, 30, 60, and 120 min using the One Touch Blood Glucose Monitoring System (LifeScan) (32).

Statistical Analysis.

All experiments were performed at least 3 times (n>3) using independent biological triplicates. Results were presented as means±SEM. All statistical tests were performed using GraphPad InStat software version 3.10. A p-value of ≤0.05 indicated statistical significance.

Example 2—Pancreatic Differentiation and Assessment of Pancreatic Markers in WT Mouse ES Cells The endocrine differentiation protocol was selected because it included RA-treatment at day 7 and also showed expression of later stage endocrine markers using human ES cells (15). The D'Amour et al. (2006) pancreatic differentiation protocol was used with some slight modifications to generate pancreatic endocrine cells in culture through the use of specific growth factors (FIG. 1A). The first modification replaced Wnt3a with BIO-acetoxime (BIO). Wnt3a has been documented as being important for mesendoderm specification and BIO-acetoxime is a selective inhibitor of GSK-3β which indirectly acts as a Wnt3a agonist during cell differentiation (33, 34). Second, nicotinamide was included during the last stage of differentiation because various published protocols included this reagent due to strong evidence for its efficacy in pancreatic differentiation (35, 36).

To characterize the impact of the differentiation protocol on pancreatic endocrine specification in WT ES cells, cellular extracts were harvested at various time points during the procedure (FIG. 1B). The mRNA levels of various differentiation markers were assessed by RT-PCR for the different experimental conditions. LIF withdrawal combined with the addition of BIO and Activin A to the culture system caused a drastic decrease in the levels of ES cell markers Nanog and Rex1 (FIG. 1B, lane 6) compared to untreated and RA-treated ES cells (FIG. 1B, lanes 1 to 4). Such a phenomenon was observed throughout the subsequent phases of the differentiation protocol (FIG. 1B, lanes 7 to 12). While robust expression of glucagon, a functional marker of α-cells (37), was observed by day-14 (FIG. 1B, lane 8), somatostatin, a hormone secreted by δ-cells (37), was detectable as early as day-5 (FIG. 1B, lane 6). Insulin-1 (β-cell marker)(37) was detected by day-11 of the differentiation protocol but its expression fluctuated depending on the uses of HGF, IGF1, or both factors together during the endocrine cell differentiation stage (FIG. 1B, lanes 9 to 11). The most consistent expression of all 3 pancreatic endocrine differentiation markers tested was observed by combining HGF and IGF1 with nicotinamide, from day-14 to 17 (FIG. 1B, lane 12). Even though keeping ES cells in culture, at confluence and in absence of LIF for 17 days, caused a decrease in Nanog and Rex1 expression, such conditions failed to induce any of the differentiation markers tested (FIG. 1B, lane 5).

These observations confirm the conversion of ES cells to endocrine cells able to express pancreatic hormone-encoding genes, according to a method described previously (15). Such a biological model represents a powerful tool to investigate the role of RARβ at specific stages of pancreatic endocrine differentiation.

Example 3—RARβ Knockout Delays Pdx1 Expression in Pancreatic Endocrine Differentiation As previously mentioned, the RA signaling, including the participation of RARβ, was suggested to be crucial for the onset of pancreatic endocrine differentiation (11, 20, 21, 24). In order to study the specific role of RARβ in such a process, WT and RARβ KO mouse ES cells were subjected to the endocrine differentiation protocol described above. RT-PCR analysis confirmed the absence of RARβ transcript in KO cells (FIG. 2A). The RARβ2 isoform, like Cyp26a1, represents a RA-inducible gene (38). This explains why stronger RARβ signal was observed in the presence of RA, in WT cells compared to untreated ones (FIG. 2A). RA-dependent Cyp26a1 expression was observed in both WT and RARβ KO ES cells, suggesting that KO cells are still responding to RA stimuli (FIG. 2A). Using this model of RARβ deletion, the inventors sought to determine the impact of such a retinoid receptor on the expression of Pdx1, which consists in a master regulator of pancreatic cell fate (39-41).

WT and RARβ KO ES cells were differentiated into pancreatic endocrine cells, as described in FIG. 1, and indirect immunofluorescence staining for Pdx1 was performed at the different stages of the protocol (FIG. 2B). Pdx1 expression was observed in WT differentiating cells by day-5, and was still present at all the other stages tested in a heterogeneous pattern (FIG. 2B). In contrast, Pdx1 protein was absent from nuclei of differencing cells at day-5 and 11, and was only detected by day-14 of the protocol in RARβ null cells (FIG. 2B).

These observations suggest that the absence of RARβ in this cell culture system undergoing pancreatic differentiation engenders a delay in the induction of Pdx1, which could potentially affect subsequent key steps of endocrine specialization.

Example 4—Absence of RARβ Expression Impairs the Global Pancreatic Endocrine Differentiation Process Considering the finding that RARβ deletion in ES cells delays the expression of Pdx1 during their specialization into pancreatic endocrine cells, the inventors decided to further investigate the impact of such a phenomenon on early, intermediate, and late molecular genetic events throughout the differentiation process. As reported in many studies on reprogramming, decreased expression of pluripotency factors, including Nanog, in ES cells is essential for proper differentiation (42). Nanog levels were previously shown to decrease around day-5 during the pancreatic endocrine differentiation protocol (FIG. 1B). A comparison of Nanog transcript levels in WT and RARβ KO differentiating cells, showed a sustained expression of this pluripotency factor in KO cells while it is severely repressed in WT controls (FIG. 3A). On the other hand, the expression of Neurogenin-3 (Ngn3), a master transcription factor during onset of pancreatic endocrine lineages (39, 41, 43), displayed a phased induction pattern in WT cells but was not induced in RARβ knockout (FIG. 3A).

Like Ngn3, Paired-box 6 (Pax6) and Islet1 (Isl-1) represent two important transcription factors in pancreatic islet cell differentiation, which are expressed from intermediate (""mid"") to terminally differentiated (""late"") stages (39, 40, 44, 45). While no difference were noted for Pax6 expression patterns, Isl-1 displayed a delayed expression peak in RARβ KO cells as compared to WT (day-14 versus day-11) (FIG. 3B).

Finally, the expression of different functional endocrine differentiation markers such as, glucagon (Gcg; α-cells), insulin-1 (Ins1; β-cells) and islet amyloid polypeptide (IAPP; β-cells) was analyzed in RARβ KO and WT differentiating cells (15, 46, 47) (FIG. 3C). In all cases, RARβ KO cells showed impaired expression of those functional markers as compared to WT (FIG. 3C). Specifically, by day-17 Gcg, Ins1, and Iapp respectively presented ~5-fold (p=0.04), ~120-fold (p=0.013), and ~7-fold (p=0.0002) increases in WT differentiated cells as compared to RARβ KO (FIG. 3C). Somatostatin (Sst), a functional marker of δ-cells (37) also displayed a decreased expression in RARβ deficient cells (not shown).

Taken together, these observations show that RARβ and retinoid signaling play a central role in pancreatic endocrine differentiation by regulating the expression of certain master genes at early and intermediate stages of the specialization process, which as a result impairs the expression of functional markers of pancreatic islet cells.

Figure 2:
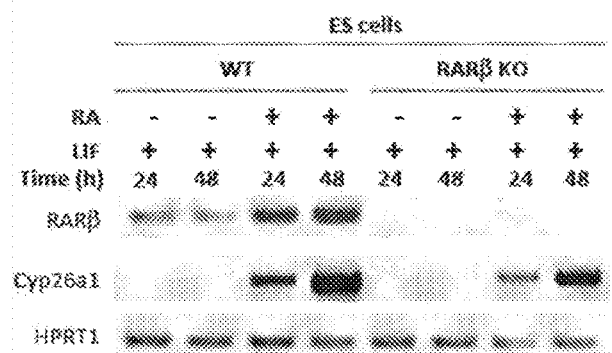
FIG. 2: Impact of RARβ deletion on Pdx1 expression through pancreatic endocrine differentiation process. (A) RT-PCR analysis confirming the suppression of RARβ in KO ES cells. Analysis of Cyp26a1, a RA-responsive gene, demonstrates the presence of RA signaling activity via other receptors in RARβ KO cells. HPRT1 was used as a control housekeeping gene. (B) Indirect immunofluorescence staining for Pdx1 (green) in WT and RARβ KO, at 5, 11, 14, and 17 days in the absence (untreated) or in the presence (treated) of growth factors used in the differentiation protocol. Cells were counterstained using rhodamine-conjugated phalloidin, which binds to F-actin (red) and nuclei were stained with DAPI (blue) (Bars=50 µm).
Figure 2:
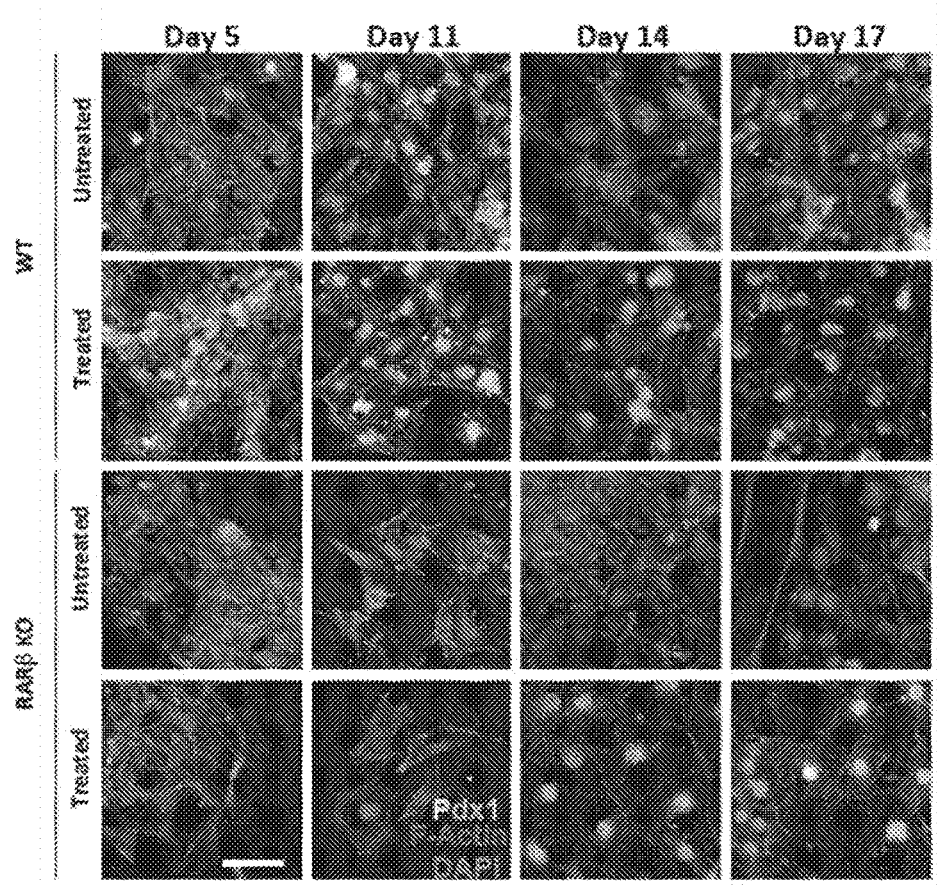
Figure 3:
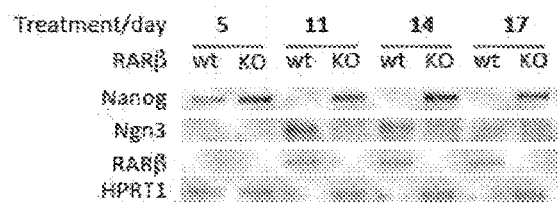
FIG. 3: Expression of pancreatic differentiation markers in WT and RARβ knockout (KO) ES cells. Transcript expression analyses of (A) early, (B) mid, and (C) late stage endocrine pancreatic differentiation markers in WT and RARβ KO ES cells. RT-PCR amplification of (A) Nanog, Ngn3, (B) Pax6, Isl-1, and (C) Ins1, Gcg, and Iapp mRNA was performed in both cell lines at 5, 11, 14, and 17 days of the differentiation protocol. In each case, RARβ expression was monitored in both cell lines and HPRT1 was used as a control housekeeping gene. Relative amounts, normalized to HPRT1 levels for each marker tested, are shown in histograms (n=3; *: $p \leq 0.05$; : $p \leq 0.0079$; *: $p \leq 0.0003$).
Figure 3:
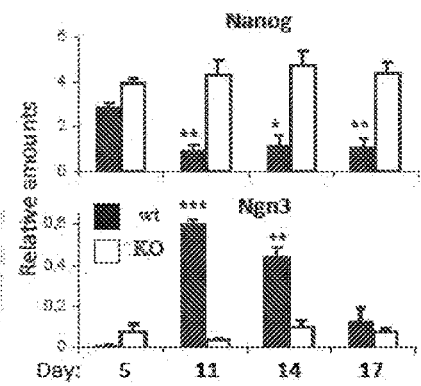
Figure 3:
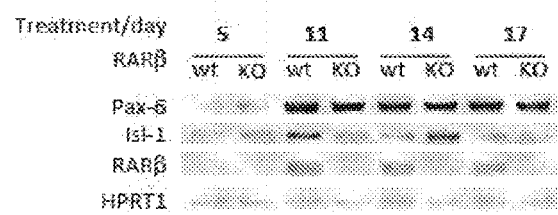
Figure 3:
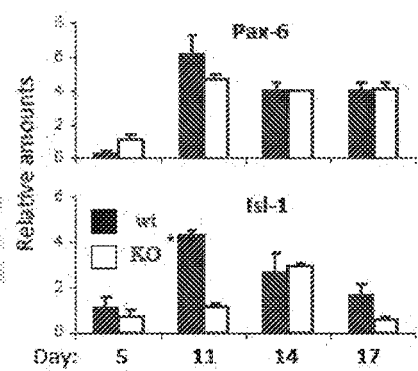
Figure 3:
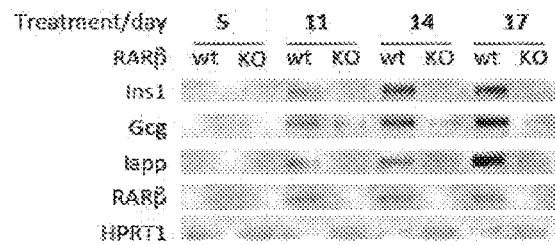
Figure 3:
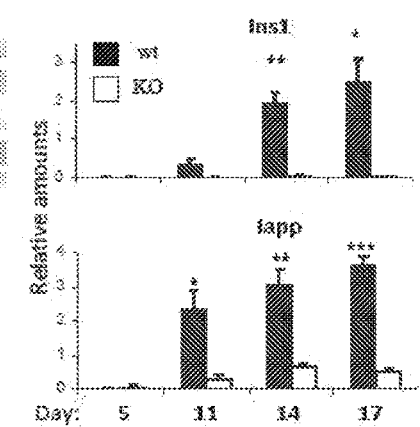

Example 5—Deletion of RARβ Affects In Vivo Glucose Metabolism and Pancreatic Islet Functionality The tissue culture system used to study diverse steps of pancreatic endocrine differentiation provided important insights about the role played by RARβ in such a physiological process. Specifically, the absence of RARβ expression leads to decreased or delayed expression of crucial transcription factors involved in islet cell differentiation, as well as decreased expression of functional differentiation markers (FIGS. 2 and 3). Thus, the inventors sought to validate the relevance of this finding in an in vivo model. A classical KO of both RARβ alleles in mice, generated and characterized by Ghyselinck et al. (26), was used to study the impact of such a deletion on pancreatic endocrine functions. By extracting pancreas from WT and RARβ-deficient mice, and performing indirect immunofluorescence staining for C-peptide, a by-product of insulin biosynthesis (48), and glucagon, the inventors observed a decrease (~75%, p<0.0001) in the size of KO mice islets as compared to WT (FIG. 4A). Western blot analysis confirmed the decrease in C-peptide and glucagon expression in RARβ KO mice pancreas extracts as compared to WT controls (FIG. 4A). These observations demonstrate that RARβ KO mice display decreased pancreatic endocrine islet cell production and/or maintenance, which could have major, deleterious effects on glucose metabolism.

To assess the systemic effects of RARβ deletion on reduced insulin and glucagon-producing cells, mice of both groups were fasted for 15 hours and blood glucose concentration was measured. While blood glucose levels in WT were normal (between 70 and 105 mg/dL) (49), RARβ KO animals were found to be in a hypoglycemic state, slightly below normal levels (61±4.7 mg/dL) (FIG. 4B) (50). In order to test the functionality of β-cells in both mice groups, a time-course blood glucose reading experiment was performed which an intraperitonial injection of 2 mg/Kg (body weight) dextrose at time ""0"". Then, blood glucose clearance was monitored at 0, 15, 30, 45, 60, and 120 minutes in WT and RARβ KO mice. We observed that blood glucose was metabolized faster in WT mice, as compared to KO (FIG. 4B). Moreover, the average blood glucose levels in RARβ KO mice 120 min after the dextrose injection was significantly higher (~30%, p=0.014) than in WT group, suggesting a lower glucose tolerance in animals lacking such a retinoid receptor (FIG. 4B).

As described in the Examples, by using an ES cell-based directed differentiation system (Examples 2-4) and an in vivo gene knockout model (Example 5), the inventors demonstrated the crucial role for RARβ in proper pancreatic endocrine cell differentiation. In both cases, the absence of RARβ led to a decrease in terminal differentiation and functional markers, such as insulin and glucagon production. In mice, RARβ deletion resulted in impaired glucose metabolism, characterized by hypoglycemia and glucose intolerance. Taken together, these findings indicate that reduced RARβ and retinoic acid signaling are key factors in glucose metabolism disorders, such as diabetes mellitus type I and II. Hence, the administration of agonists of the RARβ receptor can prevent or treat such disorders.

The study described in Example 2 leads to the conclusion that Pdx1 expression, during the pancreatic differentiation process, was delayed in the absence of RARβ (Figure-2). Such a transcription factor represents a key player in the early determination of pancreatic progenitors and bud expension (39, 40, 51, 52). A previous study reported that RA directly induces Pdx1 expression in ES cells (51). Strengthening such a statement, ChIP-chip analyses performed on F9 teratocarcinoma cells revealed the presence of a putative retinoic acid response element (RARE) located at ~3 kb upstream of the transcription start site of Pdx1 (not shown). That Pdx1 expression is delayed but not fully suppressed in RARβ-null ES cells opens a door on possible compensatory mechanisms exerted by other RARs. It has been previously noted that RARβ transcript levels are increased at stages of endocrine differentiation, while a peak of RARα expression is associated with late differentiation stages (24). Possibly RARα and β together participate in the Pdx1 biphasic expression pattern, as reviewed by Soria (39). Thus, suppressing RARβ would result exclusively in a late Pdx1 expression as observed in treated RARβ KO cells (FIG. 2).

Figure 4:
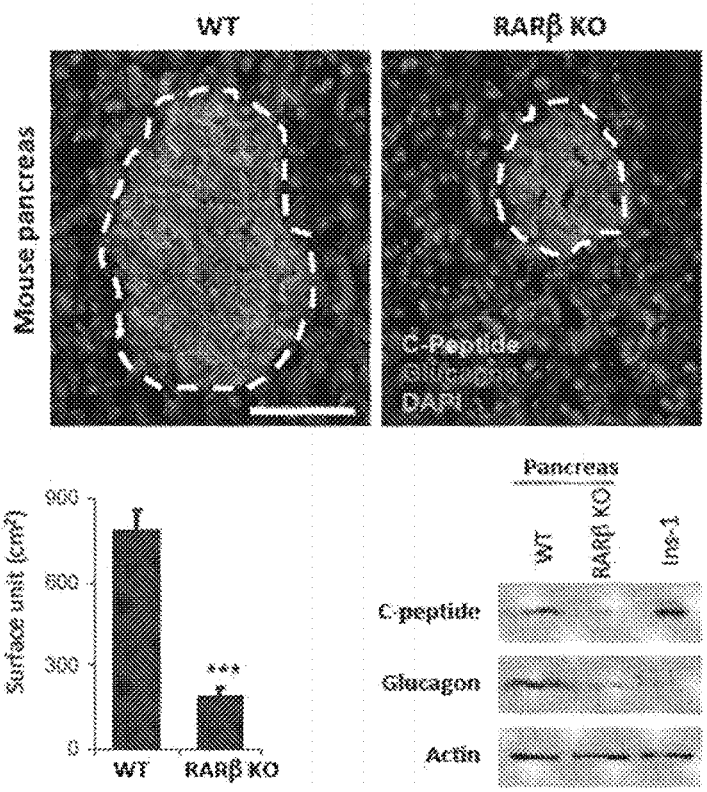
FIG. 4: In vivo characterization of RARβ deletion on islets of Langerhans functionality and glucose metabolism. (A) Indirect immunofluorescence staining of C-peptide (green) and Glucagon (red) on C57BL/6 WT and RARβ KO mouse pancreas tissue sections. Pancreatic islet-corresponding regions were circled by dashed lines and nuclei were marked with DAPI (blue) (bars=50 µm). Islet size were quantified per surface area units ($cm^2$), with respect to high resolution micrographs, for each group and presented as histogram (n=6; **: p=0.031). Western blot analysis of C-peptide and Glucagon expression was performed on WT and RARβ KO mouse pancreas protein extracts. Ins-1 cells were used as positive control for C-peptide expression, while immunodetection of actin was used as a loading control. (B) Blood glucose concentration (mg/dL) in WT and RARβ null, knockout mice after 15 h fasting (left) (n≥5; p=0.0011). Blood glucose clearance (right) for WT (♦) and RARβ KO (■) mice was measured following a 2 mg/kg dextrose i.p. injection. Relative blood glucose levels were assessed at 0, 15, 30, 45, 60, and 120 minutes post-injection (n≥6; *: p=0.0137; : $p \leq 0.0064$; *: p<0.0001).
Figure 4:
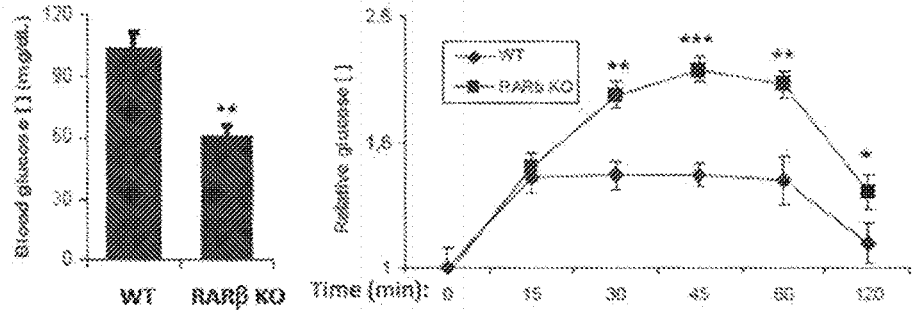

Pdx1 mis-expression was previously associated with severe β-cell dysfunction and increased cell death (53). Accordingly, RARβ KO caused a reduction in β-cell terminal differentiation markers' expression, such as Ins1 and Iapp in the cell culture system (FIG. 3), as well as a decreased number of C-peptide expressing cells in RARβ null-mice pancreatic islets (FIG. 4). Recent findings by Dalgin et al. (54) also linked RA signaling and endocrine cell fate. Although the authors claimed that β-cell progenitors differentiate as α-cells in RA downstream target mnx1 morphants, the data reported here suggest that RARβ KO induces a decrease in α-cell differentiation, characterized by reduced expression of glucagon in the cell culture system (FIG. 3) and RARβ null mice (FIG. 4). Thus, the effect observed on islet cells in the absence of RARβ could be attributed to the role of RA signaling in early pancreatic differentiation events rather than lineage-specific terminal differentiation.

Like Pdx1, the bHLH transcription factor Neurogenin3 (Ngn3) constitutes another key player in the commitment of endoderm to pancreatic precursors (40, 43, 47). Among the cascade of transcription factors involved in pancreas development, Ngn3 is the earliest to be expressed in the endocrine differentiation pathway (40, 55). While no links between RA signaling and Ngn3 expression was reported in the literature, RARβ KO cells displayed decreased levels of this transcription factor during pancreatic differentiation (FIG. 3). Thus, the impact of RARβ deletion on Ngn3 could be indirect and involving the participation of intermediate factors.

Pax6 and Isl-1 represent two major transcription factors having a role in endocrine lineage specification after bud formation (45, 56) Considering that Pax6 expression is not affected by RARβ KO, and that the Isl-1 peak of expression is only delayed by such a deletion, it appears that absence of RA signaling through RARβ is insufficient to completely abrogate endocrine differentiation, but may lead to significant defects in islet cell function.

The observations reported here indicate that the absence of RARβ expression impairs development and maintenance of pancreatic islets in vivo (FIG. 4). In mammals, glucose intolerance is characterized by sustained high blood glucose levels (above 140 mg/dL) during at least two hours, while hypoglycemia is decreed when blood concentration goes below 70 mg/dL (50, 57). Blood glucose assessment 1) after 15 h fasting and 2) upon dextrose injection led us to suggest that RAR-null mice have a predisposition to fasting hypoglycemia and increased glucose intolerance, two conditions associated with diabetes mellitus (58).

Close correlations have been made between dietary habits and diabetes, especially for type II (59). Considering the role of RAR in pancreatic endocrine cell differentiation, and that the RARβ gene itself is up-regulated by retinoic acid, a sustained vitamin A deficient diet could lead to insufficient islet cell turnover, and eventually to diabetes. RARβ expression is also known to depend on epigenetic regulation (60, 61). For instance, aberrant hypermethylation of various promoter elements was reported in different pancreatic disorders such as cancer, diabetes, and chronic pancreatitis (62-64). Therefore, epigenetic silencing of RARβ or other associated effectors could play a role in the onset of certain cases of diabetes.

The production of insulin secreting endocrine cells from ES cells using RA-based protocols is proposed as a promising tool for diabetic therapy (9). However, ensuring accurate vitamin A consumption and proper RA signaling via RARβ represent new avenues to prevent or treat diabetic disorders. In particular, the administration of an RARβ agonist would be a specifically targeted method of enhancing this RARβ signaling to prevent or treat diabetic disorders. Taken together, these findings shed light on the role of RARβ in pancreatic endocrine differentiation, which consequently affects in vivo blood glucose metabolism.

Example 6 RARβ Agonist Treatment Preparation

Preparation of AC261066 (a RARβ Agonist from Tocris) Solution.

AC261066 was dissolved in dimethyl sulfoxide (DMSO) at the concentration of 1.5 mg/ml, and diluted in the drinking water for mice to the final concentration of 1.5 mg/100 ml.

Mice, Diet, and Drug Treatment.

WT male C57/BL6 male mice were maintained on either a standard laboratory chow-fed diet (CFD) with 13% kcal fat, (diet #5053, Lab Diet, Inc, St. Louis, Mo.) or a high fat, western style diet (HFD) with 60% kcals from fat, (diet #58126, Lab Diet, Inc., St. Louis, Mo.) for 4 months. One month after the start of the high fat diet treatment, the high fat diet group was further split into 2 groups for 3 months: i) high fat diet and the drinking water containing 1% DMSO; ii) high fat diet and the drinking water containing 1.5 mg/100 ml AC261066, a specific RARβ agonist. Then mice were sacrificed by cervical dislocation. Blood and various tissue samples were harvested.

Example 7 Pancreas

Semi-Quantitate PCR.

Total RNA was extracted from mouse tissues using TRIzol reagent (Life technologies) and (1 μg) was used to synthesize cDNA. cDNA synthesis was performed at 42° C. for 1 h in a final volume of 20 μl using qScript (Quanta, MD). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows:

```
RARβ2,
                                    (SEQ ID No. 25)
F: 5'-TGGCATTGTTTGCACGCTGA-3', (SEQ ID No. 26)
R: 5'-CCCCCCTTTGGCAAAGAATAGA-3',

CYP26A1,
                                    (SEQ ID No. 27)
F: 5'-CTTTATAAGGCCGCCCAGGTTAC-3', (SEQ ID No. 28)
R: 5'-CCCGATCCGCAATTAAAGATGA-3',

LRAT,
                                    (SEQ ID No, 29)
F: 5'-TCTGGCATCTCTCCTACGCTG-3', (SEQ ID No. 30)
R: 5'-GTTCCAAGTCCTTCAGTCTCTTGC-3',

INS2,
                                    (SEQ ID No. 31)
F: 5'-TGTGGGGAGCGTGGCTTCTTCT-3', (SEQ ID No. 32)
R: 5'-CAGCTCCAGTTGTGCCACTTGT-3',

HPRT,
                                    (SEQ ID No. 33)
F: 5'-TGCTCGAGTGTGATGAAGG-3', (SEQ ID No. 34)
R: 5'-TCCCTGTTGACTGGTCATT-3'.
```

Analysis of Pancreatic Retinoids.

The frozen pancreas tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-Hydroxynonenal (4-HNE) Staining.

Paraffin-embedded sections (from two to four mice per group) were deparaffinized and rehydrated, and antigen retrieval was performed using an antigen unmasking solution (Vector Laboratories, H-3300). After quenching endogenous peroxidase with 3% $H_2O_2$, the tissue sections were blocked with the blocking reagent (from the M.O.M. kit from Vector Laboratories). Then, tissue sections were incubated with a 4-HNE antibody (1:400; mouse monoclonal antibody: Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

Retinoid Levels in Pancreatic Tissue.

Figure 5:
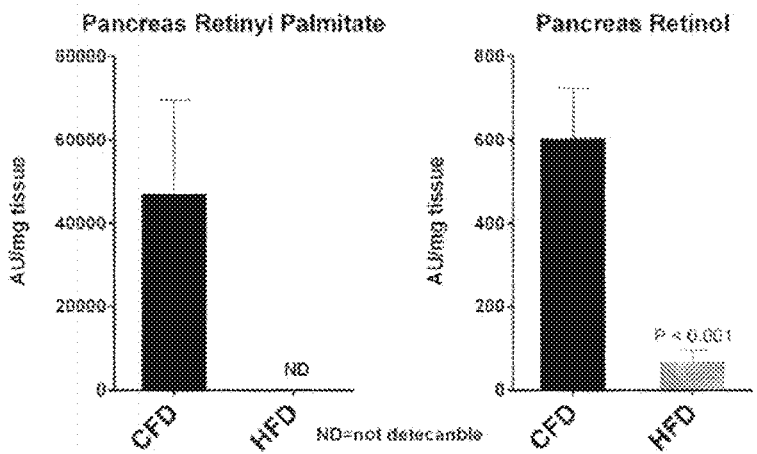
FIG. 5. Retinoid levels in mouse pancreas following the treatment indicated. Con fed diet (CFD) (n=5); HFD (n=5). Mice fed a high fat diet/obese mice have almost no retinoids in the pancreas compared to mice on a control, normal chow diet. They exhibit an organ specific vitamin A deficiency.

Our HPLC analysis revealed that that pancreata from HF-fed obese mice had dramatically decreased levels retinol (VA, vitamin A) compared to CF (control diet) controls (FIG. 5). Retinyl palmitate was undetectable in pancreata tissue from HF-fed mice (FIG. 5), showing profound pancreas vitamin A deficiency.

Serum Retinol from Mice on a High Fat Diet Vs. Control Diet Compared to the Pancreas Retinol and Retinyl Palmitate Levels from Mice on a High Fat Vs. Control Diet.

Figure 6:
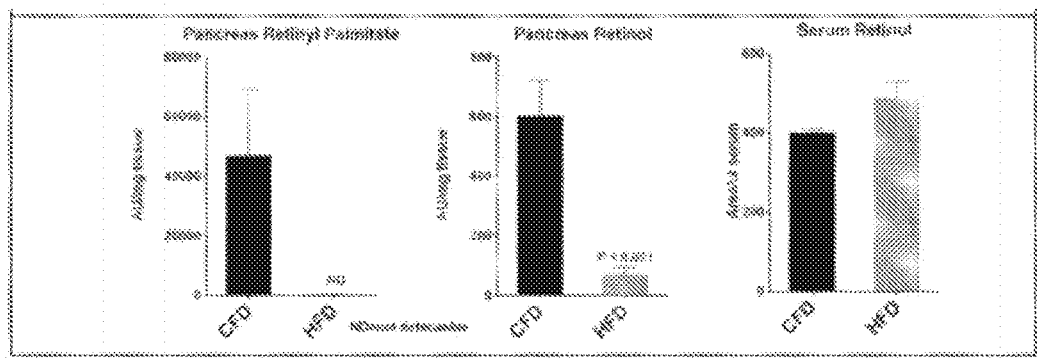
FIG. 6. Serum retinol from mice on a high fat diet vs. control diet compared to the pancreas retinol and retinyl palmitate levels from mice on a high fat vs. control diet. The serum retinol levels are similar or a bit higher in the HF diet mice, but the pancreas retinol levels are much lower in the HF diet mice, showing vitamin A deficiency in the pancreas even in the presence of normal serum vitamin A.

The serum retinol levels are similar or a bit higher in the HF diet mice, but the pancreas retinol levels are much lower in the HF diet mice, showing vitamin A deficiency in the pancreas even in the presence of normal serum vitamin A (FIG. 6).

AC261066 Decreases Oxidative Stress Levels in the Pancreas from HF-Fed Mice.

Figure 7:
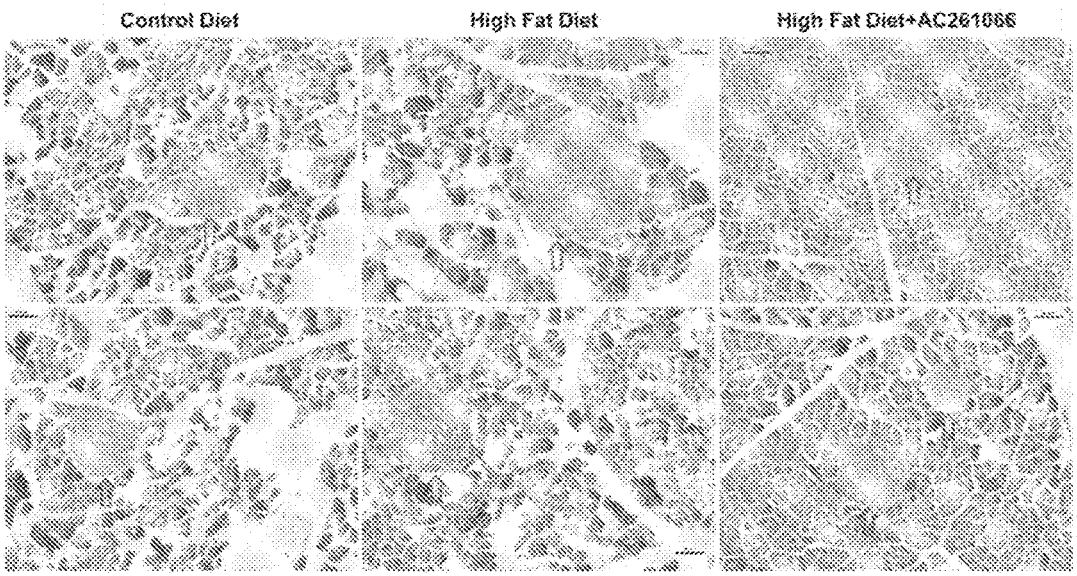
FIG. 7. 4-hydroxynonenal (4-HNE), an indicator of oxidative stress, in the pancreas. The pancreas samples were fixed, embedded in paraffin, and sectioned. Then the tissue sections were stained with an antibody against 4-HNE (magnification, 200×). Sections from two mice/group were photographed and analyzed. The arrows indicate the pancreatic islets. AC261066 reduces oxidative stress in the pancreatic islets in mice on a high fat diet(HFD+AC261066).

High fat diet results in excessive reactive oxygen species (ROS) production that triggers inflammatory responses and subsequent injuries in many tissues. Therefore, we examined the levels of 4-hydroxynonenal (4-HNE), an $\alpha,\beta$-unsaturated hydroxyalkenal that is produced by lipid peroxidation in cells during oxidative stress, and is a marker of oxidative stress caused by reactive oxygen species (ROS) in the pancreas. The pancreatic islets from HF-fed mice showed an increase in the 4-HNE levels compared to the chow-fed controls (FIG. 7). The pancreatic islet samples from the high fat diet plus AC261066 group exhibited markedly lower 4-HNE staining intensity levels compared to HF-vehicle treated mice (FIG. 7).

AC261066 does Diminish Pancreatic Islet Insulin Expression.

Figure 8:
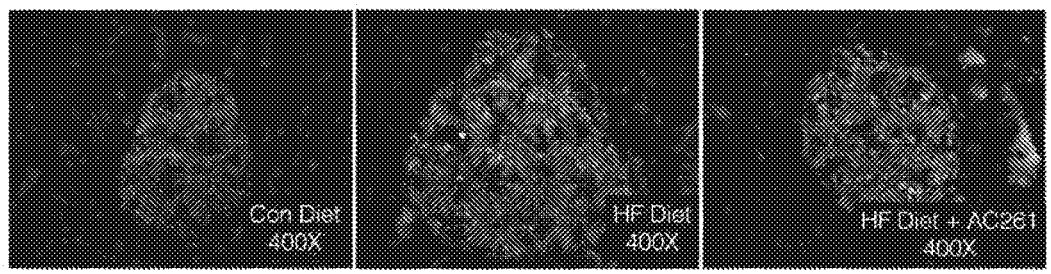
FIG. 8. AC261066 slightly reduces expression of c-peptide (marker of insulin secretion stress) in islets of HF fed mice. Representative immunofluorescence stained pancreatic sections from wild type (wt) male C57/BL6 mice fed either chow control diet (Con), high fat (HF) diet, HF diet plus AC261066 for 4 months. Con Diet (n=5); HF diet (n=5); HF Diet+AC261066 (n=5). Blue, nuclei of cells; red, glucagon; green, c-peptide.

Next we examined the changes to pancreatic expression of endocrine hormones in CF, HF and HF+AC261066 fed mice. Pancreatic islets stained for pro-insulin c-peptide (green) and glucagon (red) revealed that islets from HF and HF+AC261066 fed mice showed a marked increase in c-peptide staining compared to control diet controls (FIG. 8). AC261066 slightly decreased c-peptide level in the HF diet mice.

AC2621066 Increased Pancreatic mRNA Expression of RARβ in Obese and Vitamin a Deficient Mice.

Figure 9:
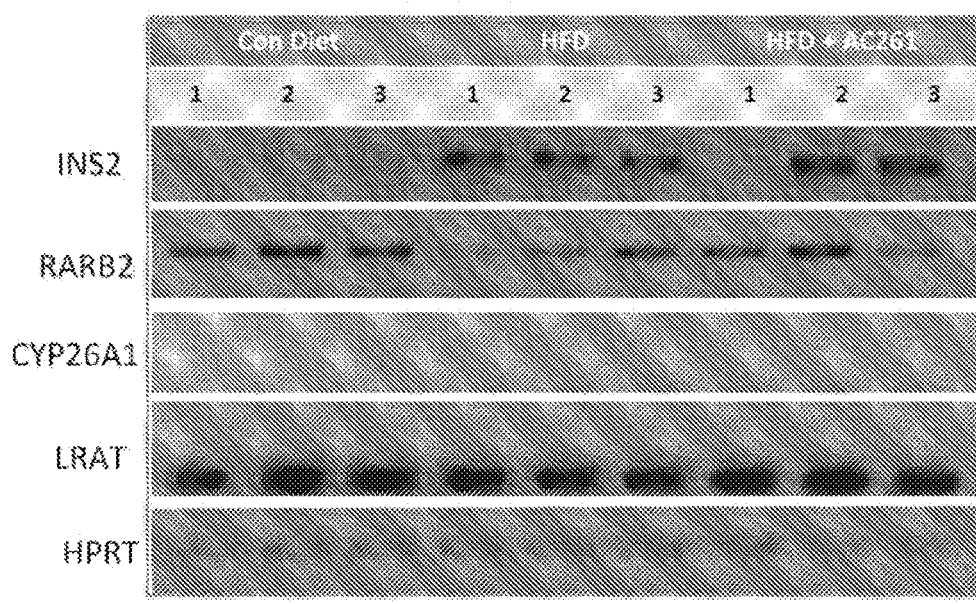
FIG. 9. Gene expression of INS2, RARβ2, CYP26A1 and LRAT in pancreatic tissue from wild type (wt) male C57/BL6 mice fed either chow control diet (Con), high fat (HF) diet, HF diet plus AC261066. Cyp26 and LRAT, no detectable signal. HPRT, loading control. RAR β2 mRNA levels were decreased by the high fat diet compared to the control diet (con), consistent with the vitamin A deficiency in the pancreas. AC261066 increased the RAR 32 mRNA levels in the HF diet mice.
Figure 10:
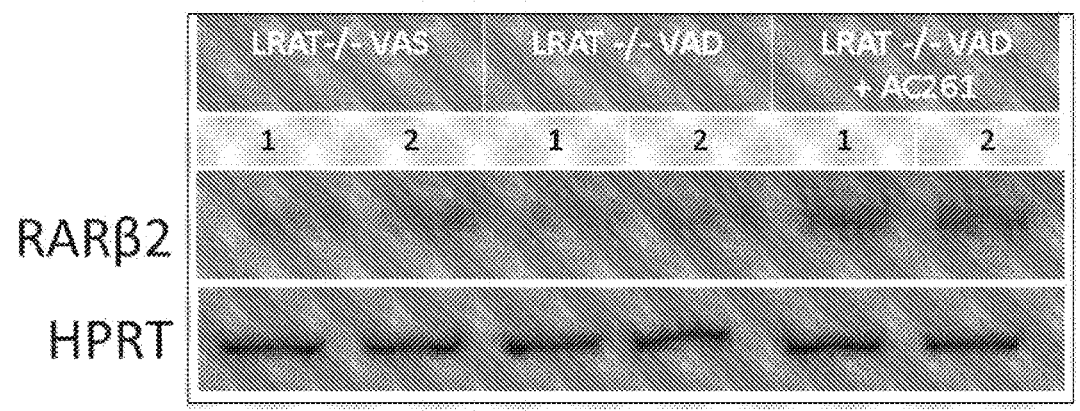
FIG. 10. Gene expression of RARβ2 in pancreatic tissue from LRAT −/− vitamin A sufficient mice (VAS, normal control diet), LRAT −/− vitamin A deficient (VAD) mice, and LRAT −/− vitamin A deficient (VAD) mice treated with AC261066 for 8 weeks. AC261066 increased the RARβ2 mRNA levels in vitamin A deficient mice (LRAT −/− on a VAD diet for 4 months.

Consistent with our HPLC data demonstrating that pancreata tissue from HF-fed, obese mice had significantly decreased VA (vitamin A) levels, and significantly decreased mRNA levels of the VA responsive gene and VA signaling transcription factor, RARβ. RAR 1 was decreased in pancreata of HF-fed obese mice compared to control diet fed mice (FIG. 9). mRNA levels of RARβ in pancreata HF-AC261066 treated mice were increased compared to HF-vehicle treated mice (FIG. 9), and near levels observed in non-obese controls, suggesting that AC261066 can prevent or reverse the loss of VA signaling in VA depleted tissue. Similar findings in vitamin A deficient mice, FIG. 10.

Example 8 Liver

Hematoxylin and Eosin Staining.

At sacrifice, fresh mouse liver samples were fixed in 4% formaldehyde solution for 24 hr and embedded in paraffin blocks. Liver paraffin sections were cut 5 microns thick and mounted on glass slides and stained with hematoxylin and eosin (H and E) using standard protocols.

Combined Oil Red O and Immunofluorescence.

Staining. Fresh mouse liver samples were embedded in optimal cutting temperature (OCT) medium and immediately frozen to −70 centigrade. Cryosections were then fixed in 4% formaldehyde for 1 hr at room temp. Slides were then rinsed three times in deionized water (dH2O) for 30 s, followed by treatment with 0.5% Triton X-100 in PBS for 5 min. Sections were then washed three times with PBS for 5 min. Samples were with incubated 2% bovine serum albumin (BSA) for 30 min at room temperature to block for unspecific antibody binding. Following blocking, sections were washed three times in PBS and incubated with mouse monoclonal antibody against α-SMA (1:500) (Dako, Inc) for 24 h at 4° C. After 24 h sections were washed three times in PB and incubated with Alexa-Flour-488 anti-mouse secondary anti-body (1:500) (Invitrogen, Inc) for 30 min at room temperature. Sections were then washed three times in PBS and incubated with working strength oil-red O solution for 30 minutes at room temperature. Sections were then rinsed for 30 minutes under running tap water and cover-slipped with Vectashield hard mount plus DAPI (Vector Labs, Inc).

Semi-Quantitate PCR (Liver).

Total RNA was extracted from mouse tissues using TRIzol reagent (Life technologies) and (1 µg) was used to synthesize cDNA. cDNA synthesis was performed at 42° C. for 1 h in a final volume of 20 µl using qScript (Quanta, MD). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved 2% agarose gels and visualized by staining with ehtidium bromide. Primers for gene expression used were as follows:

```
RARβ2,
                                        (SEQ ID No. 25)
F: 5'-TGGCATTGTTTGCACGCTGA-3', (SEQ ID No. 26)
R: 5'-CCCCCCTTTGGCAAAGAATAGA-3',

CYP26A1,
                                        (SEQ ID No. 27)
F: 5'-CTTTATAAGGCCGCCCAGGTTAC-3', (SEQ ID No. 28)
R: 5'-CCCGATCCGCAATTAAAGATGA-3',

LRAT,
                                        (SEQ ID No. 29)
F: 5'-TCTGGCATCTCTCCTACGCTG-3', (SEQ ID No. 30)
R: 5'-GTTCCAAGTCCTTCAGTCTCTTGC-3',

INS2,
                                        (SEQ ID No. 31)
F: 5'-TGTGGGGAGCGTGGCTTCTTCT-3', (SEQ ID No. 32)
R: 5'-CAGCTCCAGTTGTGCCACTTGT-3',

TNFα
                                        (SEQ ID No. 35)
F: 5'-CCTGTAGCCCACGTCGTAG-3', (SEQ ID No. 36)
R: 5'-GGGAGTAGACAAGGTACAACCC-3',

MCP1,
                                        (SEQ ID No. 37)
F: 5'-TTAAAAACCTGGATCGGAACCAA-3', (SEQ ID No. 38)
R: 5'-GCATTAGCTTCAGATTTACGGGT-3',

HPRT,
                                        (SEQ ID No. 33)
F: 5'-TGCTCGAGTGTGATGAAGG-3', (SEQ ID No. 34)
R: 5'-TCCCTGTTGACTGGTCATT-3'.
```

Serum Triglyceride Level Measurement.

The analysis of serum triglyceride levels was carried out using a bichromatic assay at the Laboratory of Comparative Pathology of the Memorial Sloan-Kettering Cancer Center. Chow-fed diet (CFD) n=2; high fat diet (HFD) n=3; high fat diet+AC261066 (HFDAC) n=5.

Analysis of Serum and Liver Retinoids.

The frozen liver tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-Hydroxynonenal (4-HNE) Staining.

Paraffin-embedded sections (from two to four mice per group) were deparaffinized and rehydrated, and antigen retrieval was performed using an antigen unmasking solution (Vector Laboratories, H-3300). After quenching endogenous peroxidase with 3% H2O2, the tissue sections were blocked with the blocking reagent (from the M.O.M. kit from Vector Laboratories). Then, tissue sections were incubated with a 4-HNE antibody (1:400; mouse monoclonal antibody; Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

Analysis of Serum and Liver Retinoids.

The frozen liver tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millenium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

AC261066 Diminished Hepatic Steatosis.

Figure 11:
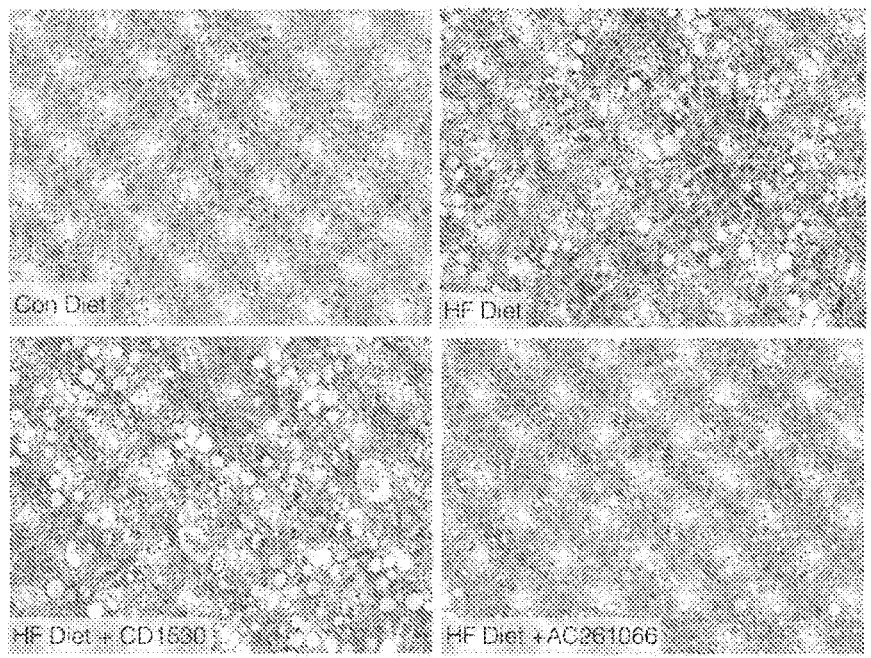
FIG. 11. AC261066 diminished hepatic steatosis. Representative hematoxylin and eosin stained liver sections from wild type (wt) male C57/BL6 mice fed either a chow control diet (Con), high fat (HF) diet, HF diet plus AC261066 or HF diet plus CD1530 (RAR gamma agonist) for 4 months. Con Diet (n=5); HF diet (n=5); HF Diet+AC261066 (n=5), or HF diet+CD1530 (RAR gamma agonist) (n=4).

H and E staining of liver sections from treatment mice revealed that 4 months of a HF western style diet lead to increased hepatocyte lipid accumulation in HF-fed mice compared to CFD-fed mice (FIG. 11). HF-fed mice treated with AC261066 showed marked decreased hepatocyte lipid infiltration compared to HF-vehicle treated mice (FIG. 11). HF-fed mice treated with a RAR γ ligand (CD1530) showed no decrease in hepatic lipid accumulation (FIG. 11).

AC261066 Diminishes Hepatic Gene Expression of Alpha-SMA (Alpha-Smooth Muscle Actin) and SREBP1c.

Figure 12:
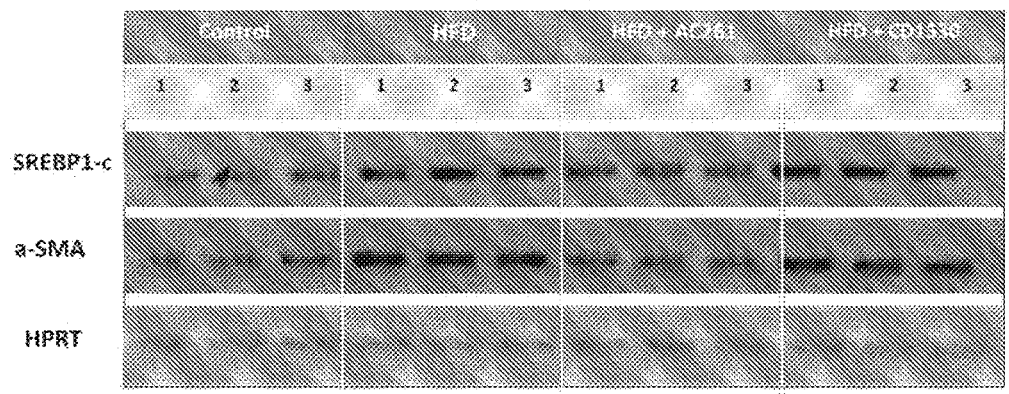
FIG. 12. Gene Expression in Livers of Control and HF-Fed Mice. Gene expression of SREBP1c and α-SMA in livers from wild type (wt) male C57/BL6 mice fed either a chow control diet (Con), high fat (HF) diet, a HF diet plus AC261066 or HF diet plus CD1530 (RAR gamma agonist) for 4 months. Con Diet (n=5): HF diet (n=5); HF Diet+AC261066 (n=5), or HF diet+CD1530 (RAR gamma agonist) (n=4).

Consistent with our immunofluorescence microscopy showing that α-SMA protein is decreased in HF-AC261011 fed mice compared to HF-vehicle controls, hepatic mRNA levels of alpha-SMA were also decreased in livers of HF-AC261011 fed mice, but not in the livers of HF-CD1530 treated mice (FIG. 12). We also measured mRNA expression of SREBP1-c, which codes for a transcription factor responsible for de novo synthesis of triglyceride and is often over-expressed in livers of animals with experimentally induced NAFLD. Our analysis revealed that mRNA levels of SREBP1-c are markedly higher in livers of HF-fed and HF-fed CD1530 treated mice, but not in livers of HF-AC261011 treated mice (FIG. 12).

AC261066 Diminishes Hepatic Stellate Cell (HSC) Activation.

Figure 13:
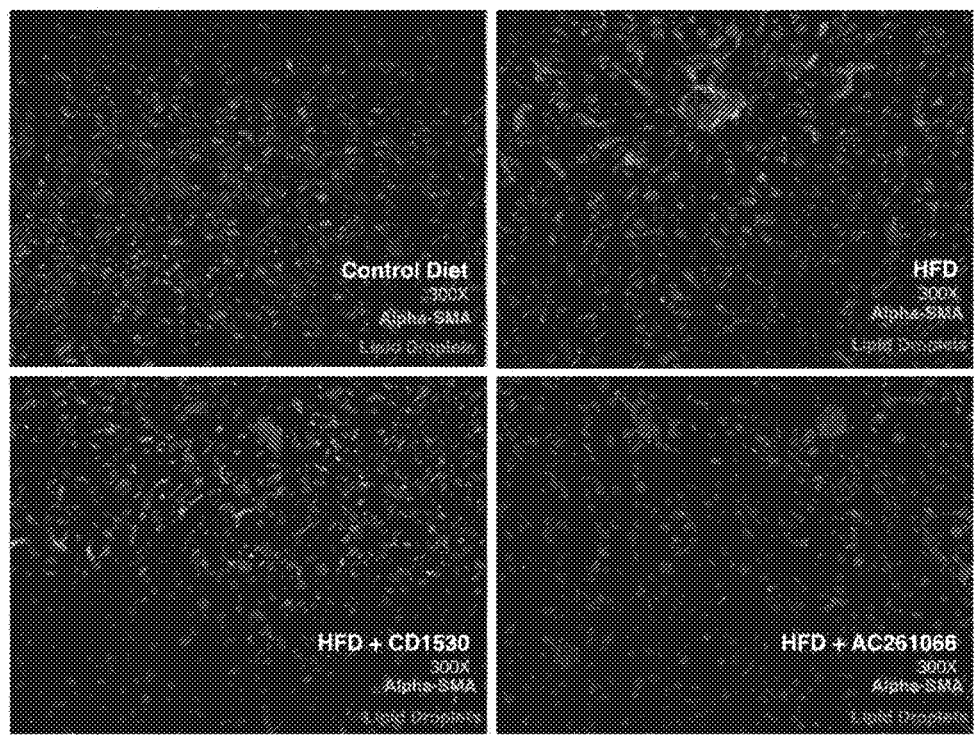
FIG. 13. AC261066 diminished activation of hepatic stellate cells. Representative immunofluorescence and oil red o stained liver sections from wild type (wt) male C57/BL6 mice fed either a chow control diet (Con), high fat (HF) diet, HF diet plus AC261066 or HF diet plus CD1530 (RAR gamma agonist) for 4 months. Control Diet (n=5); HF diet (n=5); HF Diet+AC261066 (n=5), or HF diet+CD1530 (RAR gamma agonist).

Liver sections co-stained with the neutral lipid stain oil-red-o were in agreement with the H and E staining, demonstrating that HF-fed obese mice had ectopic accumulation of hepatic lipids (red) compared to CF controls (FIG. 13). Livers of HF-AC261066-fed mice had marked diminished hepatic lipid accumulation compared to HF vehicle-fed mice (FIG. 13). This effect was not observed in the livers of HF-fed mice treated with the CD1530 (RARγ agonist).

Activated HSCs contribute to normal liver tissue repair processes, but unresolved HSC activation can lead to fibrotic lesion formation and the progression of steatosis to advanced NAFLD, such as non-alcoholic steatohepatitis (NASH). To examine whether HF-fed obese mice exhibited evidence of increased activation of HSCs we stained liver sections with an α-SMA antibody. This analysis revealed the livers of HF-fed mice had increased α-SMA positive (green) staining compared to lean, CF controls. α-SMA positive areas tended to cluster in areas with hepatocyte lipid infiltration (FIG. 13). Compared to HF-fed mice, livers of HF-fed-AC261066 treated mice had decreased intensity and regions of α-SMA positive staining (FIG. 13). Moreover, clustering α-SMA in lipid positive (red) regions was not observed in liver of HF-AC261066 treated mice. Livers of HF-fed CD1530 treated mice had no evidence decreased lipid accumulation or α-SMA expression intensity or patterns compared to HF fed-vehicle treated mice.

AC261066 Diminishes Hepatic Gene Expression of Pro-Inflammatory Mediators.

Figure 14:
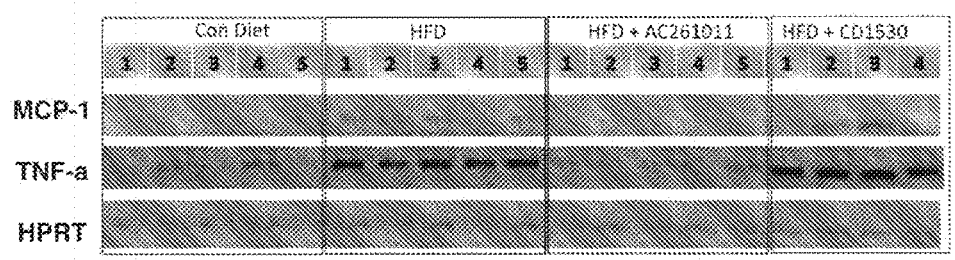
FIG. 14. Gene Expression of Inflammatory Mediators in Livers of LF and HF-Fed Mice. Gene expression of MCP-1, TNF-alpha in livers from wild type (wt) male C57/BL6 mice fed either a chow control diet (Con), high fat (HF) diet, HF diet plus AC261066 or HF diet plus CD1530 (RAR gamma agonist) for 4. LF Diet (n=5); HF diet (n=5); HF Diet+AC261066 (n=5), or HF diet+CD1530 (RAR gamma agonist) (n=4). AC261066 decreases levels of inflammatory proteins MCP-1 and TNF alpha in livers of HF diet fed mice.

NAFLD is typically associated with increased hepatic expression of pro-inflammatory cytokines and mediators such as the monocyte chemokine MCP-1 and the cytokine TNF-α. We examined expression of these genes in livers of CF and HF-fed mice. Our analysis revealed that mRNA levels of both MCP-1 and TNF-α were markedly elevated in livers of HF-fed mice HF-fed CD1530 treated mice, but not in livers of HF-fed AC261066 treated mice (FIG. 14).

AC261066 does not Elevate Serum Triglyceride Levels.

Figure 15:
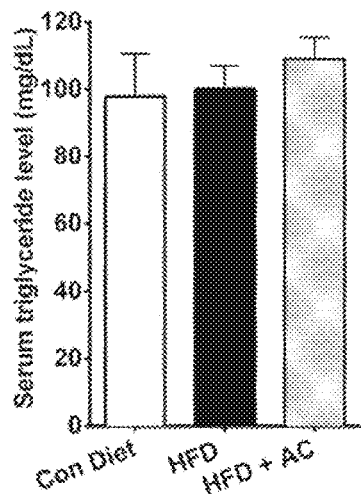
FIG. 15. Mouse serum triglyceride levels following the treatments indicated. Con diet (n=2); HFD (n=3); HFDAC (n=5). Con, control diet; HFD, high fat diet; HFD+AC, high fat diet+AC261066. AC261066 does not increase triglyceride levels at doses used.

We examined the triglyceride levels in mouse serum samples because elevated triglycerides are a risk factor for cardiovascular disease. As shown in FIG. 15, HF or HF+AC261066 feeding does not affect serum triglyceride levels compared CF controls. This suggests that AC261066 does not increase risk for cardiovascular disease and suggests that the liver lipid lowering effect of AC261066 does not correlate with increased hepatic lipid export.

AC261066 Partially Reverses Depletion of VA in Livers of HF-Fed Obese Mice.

Figure 16:
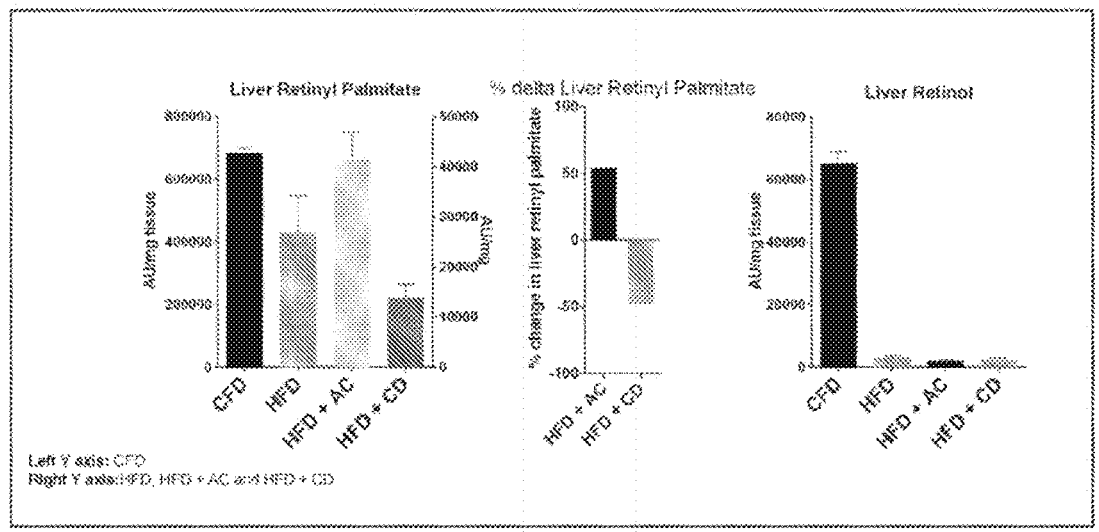
FIG. 16. Retinoid levels in mouse liver following the treatments indicated. Con fed diet (CFD) (n=5); HFD (n=5); HFD+AC261066 (n=5), HFD+CD1530 (n=4). High fat diet caused a state of vitamin A deficiency in liver and this is partially reversed by AC261066. Note that the y-axes in the left panel are different for CFD and HFD. The HFD reduced retinyl esters, (retinyl palmitate), a form of storage of vitamin A in the liver, by greater than 90% (left panel). The HFD also reduced retinol (vitamin A) levels by over 90% to result in vitamin A deficiency in the liver.

The liver stores approximately 80-90% of total body VA, therefore we conducted HPLC to determine the tissue levels of the major storage form of VA, retinyl-palmitate and of all-trans retinol in lean CF, HF and HF+AC261066 fed mice. Our analysis revealed that levels of retinyl-palmitate and retinol were decreased by 97% and 92% in livers in HF-fed, obese mice compared to lean, CF controls (FIG. 16). Serum levels of the major circulating form of VA, all-trans retinol were not different between CF, HF and HF+AC261066 fed mice, suggesting that HF-driven obesity leads to tissue VA depletion which is not reflected by serum VA levels.

Livers of mice fed HF+AC261066 and CD1530 also had significantly lowered retinyl palmitate and retinol compared to controls, however compared to HF-vehicle treated mice, we observed 55% higher levels of retinyl palmitate in the livers from HF-AC261066 fed mice, while retinyl palmitate levels in the liver of HF+CD1530 treated mice were almost 48% lower than livers from HF-vehicle treated mice (FIG. 16). This suggests that longer administration of AC261066 to HF-fed obese mice may have significantly reversed HF-obesity driven liver VA depletion.

Oxidative Stress Level as Assessed by 4-Hydroxynoneal (4-HNE), is Lower in the Liver from the High Fat Diet Plus AC261066 Group than that in the High Fat Diet Group.

Figure 17:
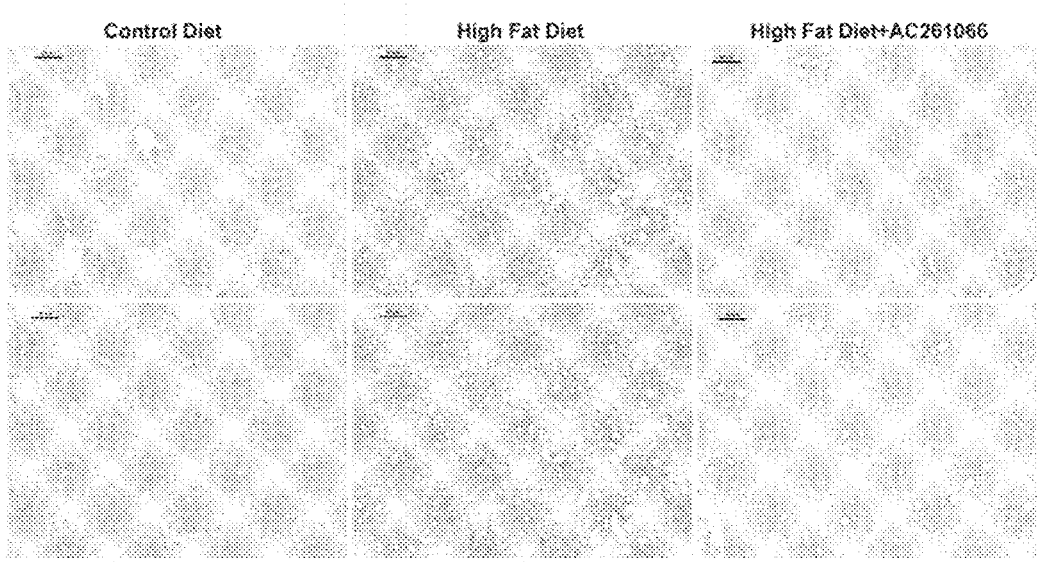
FIG. 17. 4-hydroxynonenal (4-HNE), an indicator of oxidative stress, in the liver. The liver samples were fixed, embedded in paraffin, and sectioned. Then the tissue sections were stained with an antibody against 4-HNE (magnification, 200×). Sections from two mice/group were photographed and analyzed. These data show that AC261066 reduces oxidative stress and ROS (reactive oxygen species) in the livers of HF diet fed mice. Oxidative stress damages tissues.

High fat diet results in excessive reactive oxygen species (ROS) production that triggers inflammatory responses and subsequent injuries in many tissues. Therefore, we examined the levels of 4-hydroxynonenal (4-HNE), an α,β-unsaturated hydroxyalkenal that is produced by lipid peroxidation in cells during oxidative stress, and is a marker of oxidative stress caused by reactive oxygen species (ROS) in the liver. The liver from the high fat diet group showed a large increase in the 4-HNE levels compared to the control fat diet group, and the liver samples from the high fat diet plus AC261066 group exhibited lower 4-HNE levels than those from the high fat diet group (FIG. 17).

Example 9 Kidney

Hematoxylin and Eosin Staining.

At sacrifice, fresh mouse liver samples were fixed in 4% formaldehyde solution for 24 hr and embedded in paraffin blocks. Kidney paraffin sections were cut 5 microns thick and mounted on glass slides and stained with hematoxylin and eosin (H and E) using standard protocols.

Combined Oil Red O and Immunofluorescence Staining.

Fresh mouse kidney samples were embedded in optimal cutting temperature (OCT) medium and immediately frozen to −70 centigrade. Cryosections were then fixed in 4% formaldehyde for 1 hr at room temp. Slides were then rinsed three times in deionized water (dH2O) for 30 s, followed by treatment with 0.5% Triton X-100 in PBS for 5 min. Sections were then washed three times with PBS for 5 min. Samples were with incubated 2% bovine serum albumin (BSA) for 30 min at room temperature to block for unspecific antibody binding. Following blocking, sections were washed three times in PBS and incubated with mouse monoclonal antibody against α-SMA (1:500) (Dako, Inc) for 24 h at 4° C. After 24 h sections were washed three times in PB and incubated with Alexa-Flour-488 anti-mouse secondary anti-body (1:500) (Invitrogen, Inc) for 30 min at room temperature. Sections were then washed three times in PBS and incubated with working strength oil-red O solution for 30 minutes at room temperature. Sections were then rinsed for 30 minutes under running tap water and cover-slipped with Vectashield hard mount plus DAPI (Vector Labs, Inc).

Semi-Quantitative PCR.

Total RNA was extracted from mouse tissues using TRIzol reagent (Life technologies) and (1 µg) was used to synthesize cDNA. cDNA synthesis was performed at 42° C. for 1 h in a final volume of 20 µl using qScript (Quanta, MD). Semi-quantitative PCR were performed Taq DNA polymerase (Invitrogen. CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows:

```
RARβ2,
                                    (SEQ ID No. 25)
F: 5'-TGGCATTGTTTGCACGCTGA-3', (SEQ ID No. 26)
R: 5'-CCCCCCTTTGGCAAAGAATAGA-3,

CYP26A1,
                                    (SEQ ID No. 27)
F: 5'-CTTTATAAGGCCGCCCAGGTTAC-3', (SEQ ID No. 28)
R: 5'-CCCGATCCGCAATTAAAGATGA-3',

TNFα,
                                    (SEQ ID No. 35)
F: 5'-CCTGTAGCCCACGTCGTAG-3', (SEQ ID No. 36)
R: 5'-GGGAGTAGACAAGGTACAACCC-3',

HPRT,
                                    (SEQ ID No. 33)
F: 5'-TGCTCGAGTGTGATGAAGG-3', (SEQ ID No. 34)
R: 5'-TCCCTGTTGACTGGTCATT-3'.
```

Analysis of Kidney Retinoids.

The frozen kidney tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-Hydroxynonenal (4-HNE) Staining.

Paraffin-embedded sections (from two to four mice per group) were deparaffinized and rehydrated, and antigen retrieval was performed using an antigen unmasking solution (Vector Laboratories, H-3300). After quenching endogenous peroxidase with 3% $H_2O_2$, the tissue sections were blocked with the blocking reagent (from the M.O.M. kit from Vector Laboratories). Then, tissue sections were incubated with a 4-HNE antibody (1:400; mouse monoclonal antibody; Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

AC261066 Diminished Renal Lipid Accumulation.

Figure 18:
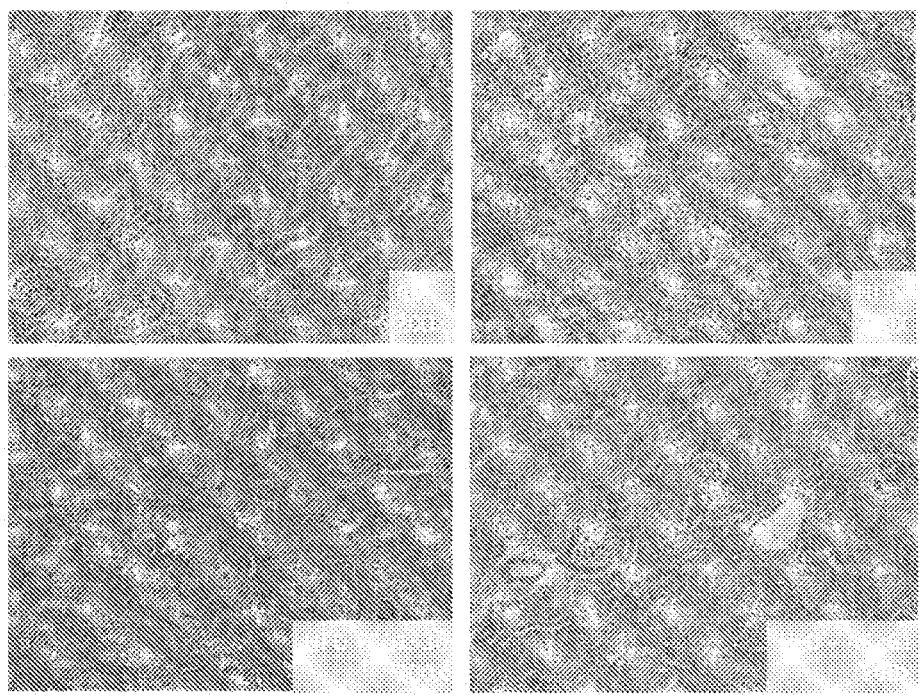
FIG. 18. AC261066 diminished renal lipid accumulation. Representative hematoxylin and eosin stained kidney sections from wild type (wt) male C57/BL6 mice fed either a chow control diet (Con), high fat (HF) diet, HF diet plus AC261066 or HF diet plus CD1530 (RAR gamma agonist) for 4 months. Con Diet (n=5): HF diet (n=5) HF Diet+ AC261066 (n=5), or HF diet+CD1530 (RAR gamma agonist) (n=4).

H and E staining of kidney sections from treatment mice revealed that 4 months of a HF western style diet lead to increased renal lipid accumulation in HF-fed mice compared to CFD-fed mice (FIG. 18). HF-fed mice treated with AC261066 showed markedly decreased renal lipid infiltration compared to HF-vehicle treated mice (FIG. 18). HF-fed mice treated with a RAR γ ligand (CD1530) showed no decrease in renal lipid accumulation (FIG. 18).

AC261066 Diminishes Renal Expression of Alpha-SMA.

Figure 19:
FIG. 19. AC261066 diminished expression of the fibrogenic protein alpha-SMA. Representative immunofluorescence and oil red o stained kidney sections from wild type (wt) male C57/BL6 mice fed either a chow control diet (Con), high fat (HF) diet, or HF diet plus AC261066 for 4 months. Chow Diet (n=5); HF diet (n=5); HF Diet+ AC261066 (n=5), or HF diet+CD1530 (RAR gamma agonist).

Kidney sections co-stained with the neutral lipid stain oil-red-o were in agreement with the H and E staining, demonstrating that HF-fed obese mice had ectopic accumulation of renal lipids (red) compared to CF controls (FIG. 18). Kidneys of HF-AC261066-fed mice had marked diminished hepatic lipid accumulation compared to HF vehicle-fed mice (FIG. 19). Alpha-SMA is required for normal kidney tissue repair processes, but unchecked alpha-SMA secretion can lead to fibrotic lesion formation and the progression of advanced renal disease. As expected kidney sections stained with the neutral lipid stain oil-red-o (red) showed marked increase in renal lipid droplets in kidneys of HF-fed mice compared to control fed mice. In agreement with our H and E histological analysis, kidney sections from HF+AC261066 treated mice had comparably less oil red o positive areas. α-SMA (green) staining also revealed that kidneys of HF-fed mice had increased α-SMA positive areas compared to control fed mice (FIG. 19). This increase in α-SMA positive areas was not observed in kidneys of HF+AC261066 treated mice.

Retinoid Levels in Kidneys.

Figure 20:
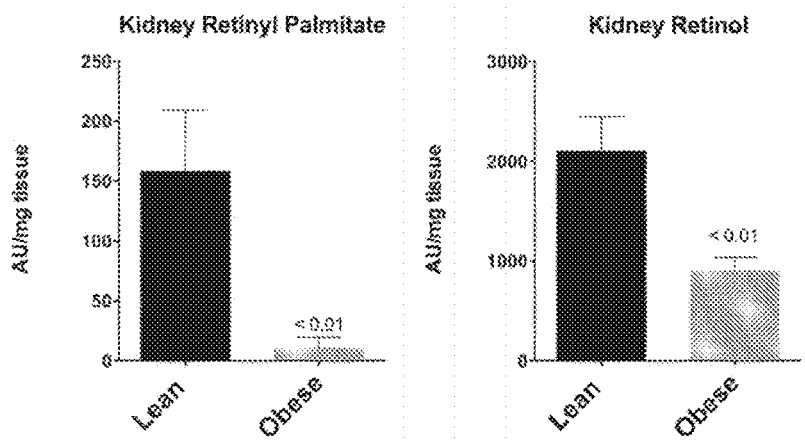
FIG. 20. Retinoid levels in mouse kidney following the treatments indicated. Con fed diet (CFD) (Lean) (n=5) or HFD (Obese)(n=5). The high fat diet led to dramatic declines in retinyl esters (retinyl palmitate) and retinol in the kidney, showing a vitamin A deficiency in kidney.

Our HPLC analysis of kidney tissue demonstrated that HF-fed obese mice had significantly decreased levels of kidney retinyl palmitate and retinol compared to chow fed controls (FIG. 20).

AC261066 Diminishes Kidney Gene Expression of Pro-Inflammatory Mediators.

Fibrosis is associated increased renal expression of pro-inflammatory cytokines and mediators. We examined whether kidneys of HF-fed mice had evidence of inflammation marked by increased expression of inflammatory cytokines such as TNF-α. Our analysis revealed that mRNA levels of TNF-α were markedly elevated in livers of HF-fed mice, but not in livers of HF-fed AC261066 treated mice (FIG. 21).

AC261066 Increased Kidney Gene Expression of RARβ2.

Figure 21:
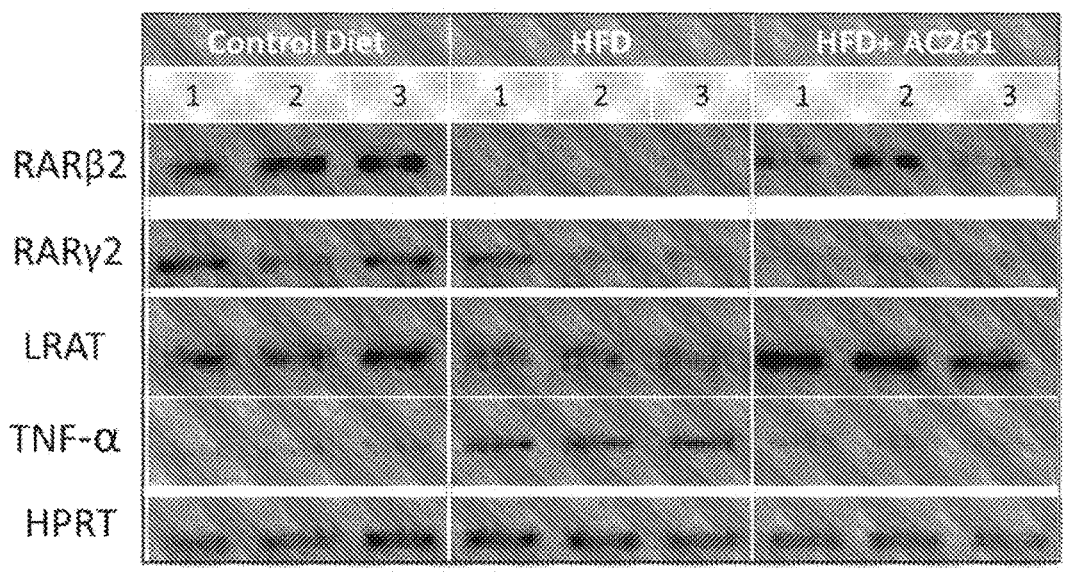
FIG. 21. Gene Expression of Inflammatory Mediators in Kidneys of Control Normal Chow (13% fat) and HF-Fed Mice and RARs. Gene expression of kidney from wild type (wt) male C57/BL6 mice fed either a chow control diet (Con), high fat (HF) diet, HF diet plus AC261066. AC261066 reduces the levels of TNF-alpha, a potent inflammatory protein, mRNA in high fat diet fed mice. AC261066 also restores RAR beta and LRAT mRNA levels, markers of functional vitamin A signaling, in the high fat diet fed mice, 4 months on the HFD. HPRT, loading control.

Consistent with the HPLC data demonstrating that VA levels are diminished in kidney of HF-fed mice, our kidney gene expression analysis revealed that RARβ2 mRNA is markedly decreased in the kidney of HF-fed mice (FIG. 21). Kidney's from HF-AC261066 did not have decreased RARβ2 mRNA levels (FIG. 21).

Oxidative Stress Level, as Assessed by 4-Hydroxynoneal (4-HNE), is Lower in the Kidneys from the High Fat Diet Plus AC261066 Group than that in the High Fat Diet Group.

Figure 22:
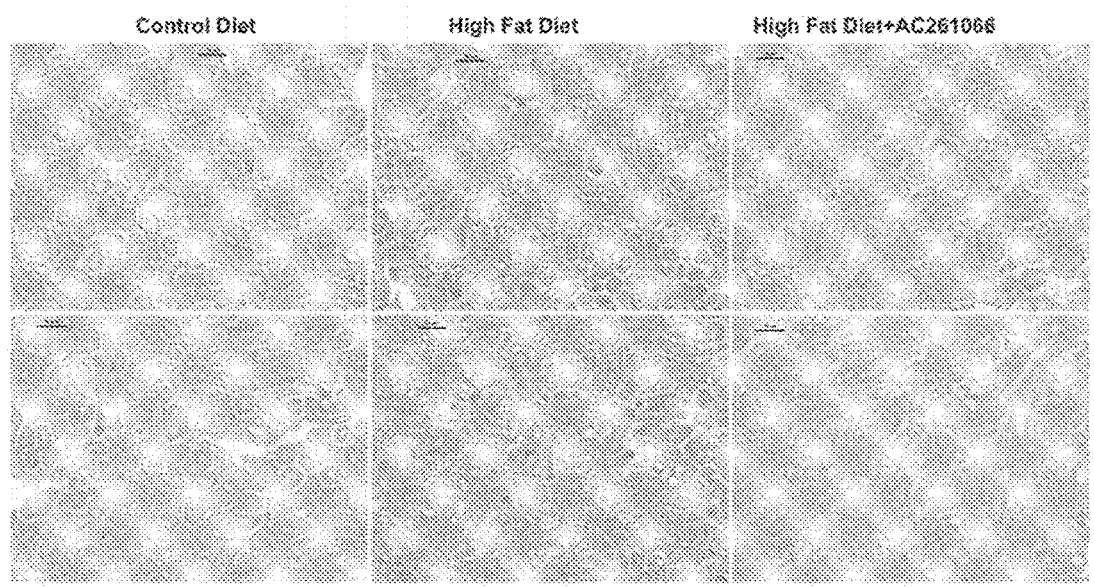
FIG. 22. 4-hydroxynonenal (4-HNE), an indicator of oxidative stress, in the kidneys. The kidney samples were fixed, embedded in paraffin, and sectioned. Then the tissue sections were stained with an antibody against 4-HNE (magnification, 200×). Sections from two mice/group were photographed and analyzed. AC261066 reduces oxidative stress (ROS) in the kidneys of mice fed the HF diet.

High fat diet results in excessive reactive oxygen species (ROS) production that triggers inflammatory responses and subsequent injuries in many tissues. Therefore, we examined the levels of 4-hydroxynonenal (4-HNE), an α,β-unsaturated hydroxyalkenal that is produced by lipid peroxidation in cells during oxidative stress, and is a marker of oxidative stress caused by reactive oxygen species (ROS) in the kidneys The kidneys from the high fat diet group showed a large increase in the 4-HNE levels compared to the control fat diet group, and the kidneys from the high fat diet plus AC261066 group exhibited lower 4-HNE levels than those from the high fat diet group (FIG. 22).

Example 10 Testes

Semi-Quantitative PCR.

Total RNA was extracted from mouse tissues using TRIzol reagent (Life technologies) and (1 µg) was used to synthesize cDNA. cDNA synthesis was performed at 42° C. for 1 h in a final volume of 20 µl using qScript (Quanta, MD). Semi-quantitative PCR were performed Taq DNA polymerase (Invitrogen, CA). Three step PCR was run as follows: 94° C. for 30 s, 58-64° C.° for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows:

```
RARβ2,
                                    (SEQ ID No. 25)
F: 5'-TGGCATTGTTTGCACGCTGA-3', (SEQ ID No. 26)
R: 5'-CCCCCCTTTGGCAAAGAATAGA-3',

CYP26A1,
                                    (SEQ ID No. 27)
F: 5'-CTTTATAAGGCCGCCCAGGTTAC-3', (SEQ ID No. 28)
R: 5'-CCCGATCCGCAATTAAAGATGA-3'
```

-continued
```
HPRT,
                                    (SEQ ID No. 33)
F: 5'-TGCTCGAGTGTGATGAAGG-3', (SEQ ID No. 34)
R: 5'-TCCCTGTTGACTGGTCATT-3'.
```

Analysis of Testes Retinoids.

The frozen kidney tissue samples (~100 mg) were homogenized in 500 µl cold phosphate-buffered saline (PBS). In addition, 100 µl serum was diluted in cold PBS to total volume of 500 pt. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

Retinoid Levels in Testes.

Figure 23:
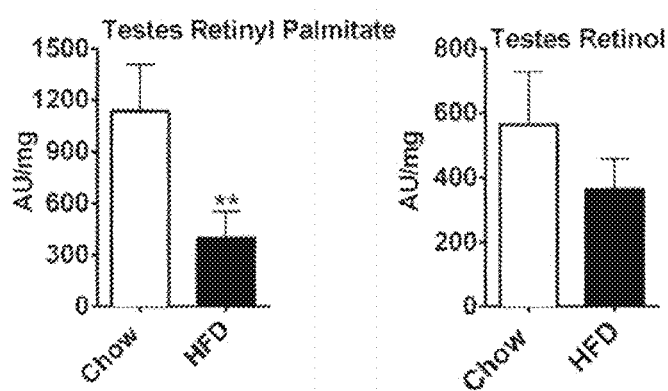
FIG. 23. Retinoid levels in mouse testes following the treatments indicated. Con fed diet (CFD) (n=5) or HFD (n=5). High fat diet results in partial vitamin A deficiency in the testes.

Our HPLC analysis of testes demonstrated that HF-fed obese mice had significantly decreased levels of retinyl palmitate (storage form of VA) and decreased retinol compared to chow fed controls (FIG. 23).

Testes of HF-Fed Mice have Decreased Expression of VA Relevant Genes Expression.

Figure 24:
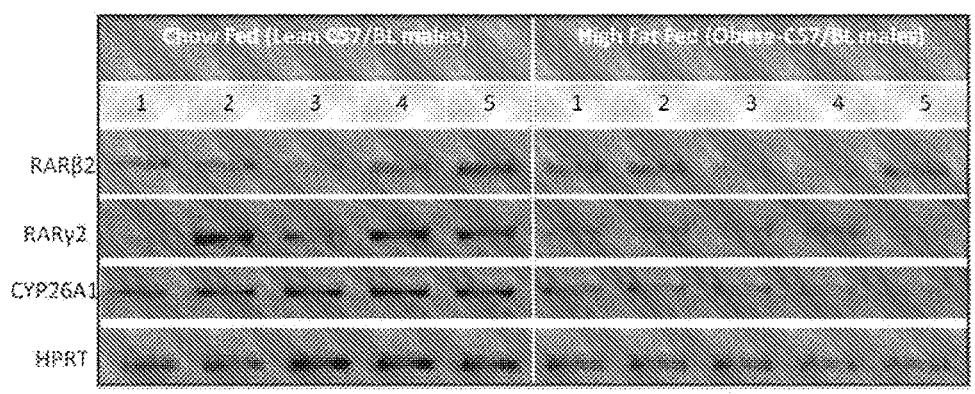
FIG. 24. Gene Expression of vitamin A relevant genes in testes of Chow and HF-Fed Mice Gene expression of testes from wild type (wt) male C57/BL6 mice fed either a chow control diet (Con), high fat (HF) diet, HF diet plus AC261066. (Each number is data from one mouse, five mice total in each group.)

Consistent with the HPLC data demonstrating that VA levels are diminished in kidney of HF-fed mice, our testes gene expression analysis revealed that RARβ2 and CYP26A1, and RAR gamma2 mRNAs are markedly decreased in the testes of HF-fed mice (FIG. 24).

RARβ agonist AC55649 is prepared in the same way and is used to treat mice as described in Examples 6-10.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

REFERENCES

1. Guariguata L. Whiting D, Weil C, Unwin N. The International Diabetes Federation diabetes atlas methodology for estimating global and national prevalence of diabetes in adults. Diabetes research and clinical practice 2011 December; 94(3):322-32.
2. Whiting D R, Guariguata L, Weil C, Shaw J. IDF diabetes atlas: global estimates of the prevalence of diabetes for 2011 and 2030. Diabetes research and clinical practice. [Research Support, Non-U.S. Gov't]. 2011 December; 94(3):311-21.
3. Huang E S, Basu A, O'Grady M, Capretta J C. Projecting the future diabetes population size and related costs for the U.S. Diabetes Care. [Research Support, N.I.H., Extramural Research Support, Non-U.S. Gov't]. 2009 December; 32(12):2225-9.
4. Oliver-Krasinski J M, Stoffers D A. On the origin of the beta cell. Genes & development. [Research Support, N.I.H., Extramural Review]. 2008 Aug. 1; 22(15):1998-2021.
5. Waldron-Lynch F, Herold K C. Immunomodulatory therapy to preserve pancreatic beta-cell function in type 1 diabetes. Nature reviews Drug discovery. [Review]. 2011 June; 10(6):439-52.
6. Waldron-Lynch F, von Herrath M, Herold K C. Towards a curative therapy in type I diabetes: remission of autoimmunity, maintenance and augmentation of beta cell mass. Novartis Foundation symposium 2008; 292:146-55; discussion 55-8, 202-3.
7. Charbonnel B, Penfornis A, Varroud-Vial M, Kusnik-Joinville O, Detournay B. Insulin therapy for diabetes mellitus: Treatment regimens and associated costs. Diabetes & metabolism 2011 Dec. 13.
8. Soria B, Andreu E, Berná G, Fuentes E, Gil A, León-Quinto T, Martin F, Montanya E, Nadal A, Reig J A, Ripoll C, Roche E, Sanchez-Andrés J V, Segura J. Engineering pancreatic islets. Pflügers Archiv—European Journal of Physiology 2000; 440(1):1-18.
9. Zaret K S, Grompe M. Generation and regeneration of cells of the liver and pancreas. Science. [Research Support, N.I.H., Extramural Research Support, Non-U.S. Gov't Review]. 2008 Dec. 5; 322(5907):1490-4.
10. Weir G C, Cavelti-Weder C, Bonner-Weir S. Stem cell approaches for diabetes: towards beta cell replacement. Genome medicine 2011; 3(9):61.
11. Sui J, Mehta M, Shi B, Morahan G, Jiang F X. Directed Differentiation of Embryonic Stem Cells Allows Exploration of Novel Transcription Factor Genes for Pancreas Development. Stem cell reviews 2012 Jan. 26; 1(1):1-10.
12. Ben-Yehudah A, White C, Navara C S, Castro C A, Ize-Ludlow D, Shaffer B, Sukhwani M, Mathews C E, Chaillet J R, Witchel S F. Evaluating protocols for embryonic stem cell differentiation into insulin-secreting beta-cells using insulin II-GFP as a specific and noninvasive reporter. Cloning Stem Cells 2009 June; 11(2):245-57.
13. Blyszczuk P, Czyz J., Kania G, Wagner M. Roll U, St-Onge L, Wobus A M. Expression of Pax4 in embryonic stem cells promotes differentiation of nestin-positive progenitor and insulin-producing cells. Proc Natl Acad Sci USA. [Research Support, Non-U.S. Gov't]. 2003 Feb. 4; 100(3):998-1003.
14. Borowiak M, Maehr R, Chen S, Chen A E, Tang W, Fox J L, Schreiber S L, Melton D A. Small molecules efficiently direct endodermal differentiation of mouse and human embryonic stem cells. Cell Stem Cell 2009 Apr. 3; 4(4):348-58.
15. D'Amour K A, Bang A G, Eliazer S, Kelly O G, Agulnick A D, Smart N G, Moorman M A, Kroon E, Carpenter M K, Baetge E E. Production of pancreatic hormone-expressing endocrine cells from human embryonic stem cells. Nat Biotechnol. [Research Support, Non-U.S. Gov't]. 2006 November; 24(11):1392-401.
16. Kroon E, Martinson L A, Kadoya K, Bang A G, Kelly O G, Eliazer S, Young H, Richardson M, Smart N G, Cunningham J, Agulnick A D, D'Amour K A, Carpenter M K, Baetge E E. Pancreatic endoderm derived from human embryonic stem cells generates glucose-responsive insulin-secreting cells in vivo. Nat Biotechnol 2008 April; 26(4):443-52.
17. Micallef S J, Janes M E, Knezevic K, Davis R P, Elefanty A G, Stanley E G. Retinoic acid induces Pdx1-positive endoderm in differentiating mouse embryonic stem cells. Diabetes 2005 February; 54(2):301-5.
18. Laursen K B, Wong P M, Gudas L J. Epigenetic regulation by RARalpha maintains ligand-independent transcriptional activity. Nucleic acids research 2012 January; 40(1):102-15.
19. Jaramillo M, Banerjee I. Endothelial cell co-culture mediates maturation of human embryonic stem cell to pancreatic insulin producing cells in a directed differentiation approach. J Vis Exp 2012(61).
20. Chen Y, Pan F C, Brandes N, Afelik S, Solter M, Pieler T. Retinoic acid signaling is essential for pancreas development and promotes endocrine at the expense of exocrine cell differentiation in Xenopus. Developmental biology. [Comparative Study Research Support, Non-U.S. Gov't]. 2004 Jul. 1; 271(1):144-60.
21. Ostrom M, Loffler K A, Edfalk S, Selander L, Dahl U, Ricordi C, Jeon J, Correa-Medina M, Diez J, Edlund H. Retinoic acid promotes the generation of pancreatic endocrine progenitor cells and their further differentiation into beta-cells. PloS One. [Research Support, Non-U.S. Gov't]. 2008; 3(7):e2841.
22. Matthews K A, Rhoten W B, Driscoll H K, Chertow B S. Vitamin A deficiency impairs fetal islet development and causes subsequent glucose intolerance in adult rats. The Journal of nutrition. [Research Support, U.S. Gov't, P.H.S.]. 2004 August; 134(8):1958-63.
23. Chertow B S, Blaner W S, Baranetsky N G, Sivitz W I, Cordle M B, Thompson D, Meda P. Effects of vitamin A deficiency and repletion on rat insulin secretion in vivo and in vitro from isolated islets. J Clin Invest. [In Vitro Research Support, Non-U.S. Gov't Research Support, U.S. Gov't, P.H.S.]. 1987 January; 79(1):163-9.
24. Dodge R, Loomans C, Sharma A, Bonner-Weir S. Developmental pathways during in vitro progression of human islet neogenesis. Differentiation. [Research Support, N.I.H., Extramural Research Support, Non-U.S. Gov't]. 2009 February; 77(2):135-47.
25. Dolle P, Ruberte E, Leroy P, Morriss-Kay G, Chambon P. Retinoic acid receptors and cellular retinoid binding proteins. I. A systematic study of their differential pattern of transcription during mouse organogenesis. Development. [Research Support, Non-U.S. Gov't]. 1990 December; 110(4):1133-51.
26. Ghyselinck N B, Dupe V. Dierich A, Messaddeq N, Gamier J M, Rochette-Egly C, Chambon P, Mark M. Role of the retinoic acid receptor beta (RARβ) during mouse development. The International journal of developmental biology. [Research Support, Non-U.S. Gov't Research Support, U.S. Gov't, P.H.S.]. 1997 June; 41(3):425-47.
27. Martinez-Ceballos E, Gudas L J. Hoxal is required for the retinoic acid-induced differentiation of embryonic stem cells into neurons. Journal of neuroscience research. [Research Support, N.I.H., Extramural]. 2008 October; 86(13):2809-19.
28. Martinez-Ceballos E, Chambon P, Gudas L J. Differences in gene expression between wild type and Hoxal knockout embryonic stem cells after retinoic acid treatment or leukemia inhibitory factor (LIF) removal. The Journal of biological chemistry. [Research Support, N.I.H., Extramural Research Support, U.S. Gov't, P.H.S.]. 2005 Apr. 22; 280(16):16484-98.
29. Benoit Y D, Lussier C, Ducharme P A, Sivret S, Schnapp L M, Basora N, Beaulieu J F. Integrin alpha8beta1 regulates adhesion, migration and proliferation of human intestinal crypt cells via a predominant RhoA/ROCK-dependent mechanism. Biology of the cell/under the auspices of the European Cell Biology Organization. [Research Support, Non-U.S. Gov't]. 2009 December; 101(12):695-708.
30. Benoit Y D, Pare F, Francoeur C, Jean D, Tremblay E, Boudreau F, Escaffit F, Beaulieu J F. Cooperation between HNF-1alpha, Cdx2, and GATA-4 in initiating an enterocytic differentiation program in a normal human intestinal epithelial progenitor cell line. American journal of physiology Gastrointestinal and liver physiology. [Research Support, Non-U.S. Gov't]. 2010 April; 298(4):G504-17.
31. Auclair B A, Benoit Y D, Rivard N, Mishina Y, Perreault N. Bone morphogenetic protein signaling is essential for terminal differentiation of the intestinal secretory cell lineage. Gastroenterology 2007 September; 133(3):887-96.
32. Yoshino J, Mills K F, Yoon M J, Imai S. Nicotinamide mononucleotide, a key NAD(+) intermediate, treats the pathophysiology of diet- and age-induced diabetes in mice. Cell Metab 2011 Oct. 5; 14(4):528-36.
33. Spokoini R, Kfir-Erenfeld S, Yefenof E, Sionov R V. Glycogen synthase kinase-3 plays a central role in mediating glucocorticoid-induced apoptosis. Mol Endocrinol 2010 June; 24(6):1136-50.
34. Yamaguchi T P, Takada S, Yoshikawa Y, Wu N, McMahon A P. T (Brachyury) is a direct target of Wnt3a during paraxial mesoderm specification. Genes & development 1999 Dec. 15; 13(24):3185-90.
35. Otonkoski T, Beattie G M, Mally M I, Ricordi C, Hayek A. Nicotinamide is a potent inducer of endocrine differentiation in cultured human fetal pancreatic cells. J Clin Invest 1993 September; 92(3):1459-66.
36. Lumelsky N, Blondel O, Laeng P, Velasco L Ravin R, McKay R. Differentiation of embryonic stem cells to insulin-secreting structures similar to pancreatic islets. Science. [Research Support, Non-U.S. Gov't]. 2001 May 18; 292(5520):1389-94.
37. Marchand M, Schroeder I S, Markossian S. Skoudy A, Negre D, Cosset F L, Real P, Kaiser C, Wobus A M, Savatier P. Mouse E S cells over-expressing the transcription factor NeuroD1 show increased differentiation towards endocrine lineages and insulin-expressing cells. The International journal of developmental biology. [Research Support, Non-U.S. Gov't]. 2009; 53(4):569-78.
38. Langton S, Gudas L J. CYP26A1 knockout embryonic stem cells exhibit reduced differentiation and growth arrest in response to retinoic acid. Developmental biology. [Research Support, N.I.H., Extramural Research Support, U.S. Gov't, Non-P.H.S.]. 2008 Mar. 15; 315(2):331-54.
39. Soria B. In-vitro differentiation of pancreatic beta-cells. Differentiation 2001 October; 68(4-5):205-19.
40. Van Hoof D, D'Amour K A, German M S. Derivation of insulin-producing cells from human embryonic stem cells. Stem cell research. [Research Support, Non-U.S. Gov't Review]. 2009 September-November; 3(2-3):73-87.
41. Bernardo A S, Hay C W, Docherty K. Pancreatic transcription factors and their role in the birth, life and survival of the pancreatic beta cell. Mol Cell Endocrinol 2008 Nov. 6; 294(1-2):1-9.
42. Kashyap V, Rezende N C, Scotland K B, Shaffer S M, Persson J L., Gudas L J, Mongan N P. Regulation of stem cell pluripotency and differentiation involves a mutual regulatory circuit of the NANOG, OCT4, and SOX2 pluripotency transcription factors with polycomb repressive complexes and stem cell microRNAs. Stem cells and development 2009 September; 18(7): 1093-108.
43. Rukstalis J M, Habener J F. Neurogenin3: a master regulator of pancreatic islet differentiation and regeneration. Islets 2009 November-December; 1(3):177-84.
44. Gosmain Y, Katz L S, Masson M H, Cheyssac C, Poisson C, Philippe J. Pax6 is crucial for beta-cell function, insulin biosynthesis, and glucose-induced insulin secretion. Mol Endocrinol. [Research Support, Non-U.S. Gov't]. 2012 April; 26(4):696-709.
45. Ahlgren U, Pfaff S L, Jessell T M, Edlund T, Edlund H. Independent requirement for ISL1 in formation of pancreatic mesenchyme and islet cells. Nature. [Research Support, Non-U.S. Gov't]. 1997 Jan. 16; 385(6613):257-60.
46. Naujok O, Francini F, Picton S, Bailey C J, Lenzen S, Jorns A. Changes in gene expression and morphology of mouse embryonic stem cells on differentiation into insulin-producing cells in vitro and in vivo. Diabetes Metab Res Rev 2009 July; 25(5):464-76.
47. Gasa R, Mrejen C, Leachman N, Otten M, Barnes M, Wang J, Chakrabarti S, Mirmira R, German M. Proendocrine genes coordinate the pancreatic islet differentiation program in vitro. Proc Natl Acad Sci USA 2004 Sep. 7; 101(36):13245-50.
48. Steiner D F, Cunningham D, Spigelman L, Aten B. Insulin biosynthesis: evidence for a precursor. Science 1967 Aug. 11; 157(3789):697-700.
49. Daly M E, Vale C, Walker M, Littlefield A, Alberti K G, Mathers J C. Acute effects on insulin sensitivity and diurnal metabolic profiles of a high-sucrose compared with a high-starch diet. Am J Clin Nutr 1998 June; 67(6):1186-96.
50. Cryer P E, Axelrod L, Grossman A B, Heller S R, Montori V M, Seaquist E R, Service F J. Evaluation and management of adult hypoglycemic disorders: an Endocrine Society Clinical Practice Guideline. The Journal of clinical endocrinology and metabolism 2009 March; 94(3):709-28.
51. Cai J, Yu C, Liu Y, Chen S, Guo Y, Yong J, Lu W, Ding M, Deng H. Generation of homogeneous PDX1(+) pancreatic progenitors from human E S cell-derived endoderm cells. J Mol Cell Biol. [Research Support, Non-U.S. Gov't]. 2010 February; 2(1):50-60.
52. Jonsson J, Carlsson L, Edlund T, Edlund H. Insulin-promoter-factor 1 is required for pancreas development in mice. Nature 1994 Oct. 13; 371(6498):606-9.
53. Fujimoto K, Polonsky K S. Pdx1 and other factors that regulate pancreatic beta-cell survival. Diabetes, obesity & metabolism 2009 November; 11 Suppl 4:30-7.
54. Dalgin G, Ward A B, Hao le T, Beattie C E, Nechiporuk A, Prince V E. Zebrafish mnx1 controls cell fate choice in the developing endocrine pancreas. Development 2011 November; 138(21):4597-608.
55. Vetere A, Marsich E, Di Piazza M, Koncan R, Micali F, Paoletti S. Neurogenin3 triggers beta-cell differentiation of retinoic acid-derived endoderm cells. The Biochemical journal 2003 May 1; 371(Pt 3):831-41.
56. Dohrmann C, Gruss P, Lemaire L. Pax genes and the differentiation of hormone producing endocrine cells in the pancreas. Mech Dev 2000 Mar. 15; 92(1):47-54.

57. American Diabetes A. Diagnosis and classification of diabetes mellitus. Diabetes Care 2005 January; 28 Suppl 1:S37-42.
58. Del Prato S, Marchetti P. Beta- and alpha-cell dysfunction in type 2 diabetes. Horm Metab Res 2004 November-December; 36(11-12):775-81.
59. Riserus U, Willett W C, Hu F B. Dietary fats and prevention of type 2 diabetes. Prog Lipid Res 2009 January; 48(1):44-51.
60. Sirchia S M, Ren M, Pili R, Sironi E, Somenzi G, Ghidoni R. Toma S, Nicolo G, Sacchi N. Endogenous reactivation of the RARβ2 tumor suppressor gene epigenetically silenced in breast cancer. Cancer research 2002 May 1; 62(9):2455-61.
61. Youssef E M, Estecio M R. Issa J P. Methylation and regulation of expression of different retinoic acid receptor beta isoforms in human colon cancer. Cancer Biol Ther 2004 January; 3(1):82-6.
62. House M G, Herman J G, Guo M Z, Hooker C M, Schulick R D, Lillemoe K D, Cameron J L, Hruban R H, Maitra A, Yeo C J. Aberrant hypermethylation of tumor suppressor genes in pancreatic endocrine neoplasms. Ann Surg 2003 September; 238(3):423-31; discussion 31-2.
63. Sato N, Fukushima N, Hruban R H, Goggins M. CpG island methylation profile of pancreatic intraepithelial neoplasia. Mod Pathol 2008 March; 2 (3):238-44.
64. Volkmar M. Dedeurwaerder S, Cunha D A, Ndlovu M N, Defrance M, Deplus R, Calonne E, Volkmar U, Igoillo-Esteve M, Naamane N, Del Guerra S, Masini M, Bugliani M, Marchetti P, Cnop M, Eizirik D L, Fuks F. DNA methylation profiling identifies epigenetic dysregulation in pancreatic islets from type 2 diabetic patients. EMBO J2012 Mar. 21; 31(6):1405-26.
65. Lund, B. W.; Piu, F.; Gauthier, N. K.; Eeg, A.; Currier, E.; Sherbukhin, V.; Brann, M. R.; Hacksell, U.; Olsson. R. Discovery of a Potent, Orally Available, and Isoform-Selective Retinoic Acid beta2 Receptor Agonist. J. Med. Chem. 2005, 48, 7517-7519
66. Vivat-Hannah V et al, Synergistic Cytotoxicity Exhibited by Combination Treatment of Selective Retinoid Ligands with Taxol (Paclitaxel). Cancer Res. 2001, 61, 8703-8711.
67. Millikan L E, Adapalene: an update on newer comparative studies between the various retinoids. Int. J. Dermatol. 2000, 39, 784-88.
68. Chen J Y et al (1995) RAR-specific agonist/antagonists which dissociate transactivation and API transrepression inhibit anchorage-independent cell proliferation. EMBO J. 1995, 14, 1187-97.
69. Lazo M, Hernaez R, Eberhardt M S, Bonekamp S, Kamel I, Guallar E, Koteish A, Brancati F L, Clark J M. Prevalence of nonalcoholic fatty liver disease in the United States: the Third National Health and Nutrition Examination Survey, 1988-1994. Am J Epidemiol. 2013; 1:38-45.
70. Loomba R, Sanyal A J. The global NAFLD epidemic. Nat Rev Gastroenterol Hepatol. 2013; 11:686-90.
71. Baffy G, Brunt E M, Caldwell S L. Hepatocellular carcinoma in non-alcoholic fatty liver disease: an emerging menace. J Hepatol. 2012; 6:1384-91.
72. Reeves H L, Friedman S L. Activation of hepatic stellate cells—a key issue in liver fibrosis. Front Biosci. 2002; 7:808-26
73. Puche J E, Saiman Y, Friedman S L. Hepatic stellate cells and liver fibrosis. Compr Physiol. 2013; 4):1473-92.
74. Geerts, A. History, heterogeneity, developmental biology, and functions of quiescent hepatic stellate cells. Semin. Liver Dis. 2001; 21:311-335
75. Brun P J, Yang K J, Lee S A, Yuen J J, Blaner W S. Retinoids: Potent regulators of metabolism. Biofactors. 2013 2):151-63.

---

What is claimed is:

1. A method of treating a pancreatic disease associated with reduced vitamin A levels in the pancreas in a subject in need thereof, the method comprising administering to said subject a pharmaceutical composition comprising an agonist of retinoic acid receptor-beta (RARβ), wherein said agonist is a compound set forth in Formula I, a compound set forth in Formula II,

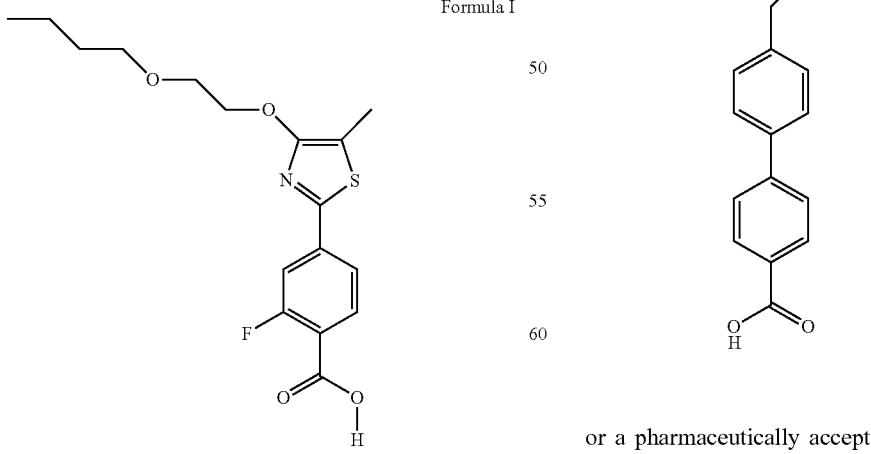

or a pharmaceutically acceptable salt, and wherein said pharmaceutical composition further comprising a pharmaceutically acceptable carrier, thereby treating said disease in said subject.

2. The method of claim 1, wherein said pancreatic disease is diabetes.

3. The method of claim 2, wherein said diabetes is type I or type II diabetes, or gestational diabetes.

4. The method of claim 1, wherein said pharmaceutical composition comprises both of said compound set forth in Formula I and said compound set forth in Formula II.

5. A method of treating liver disease associated with reduced vitamin A levels in the liver in a subject in need thereof, the method comprising administering to said subject a pharmaceutical composition comprising an agonist of retinoic acid receptor-beta (RARβ), wherein said agonist is a compound set forth in Formula I,

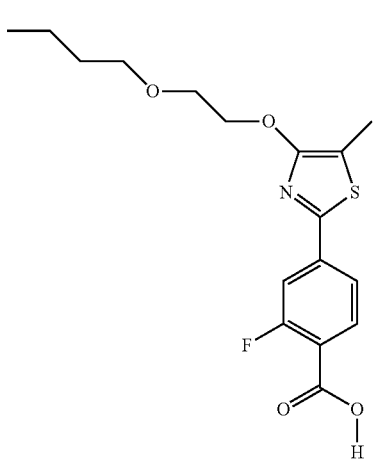

Formula I a compound set forth in Formula II,

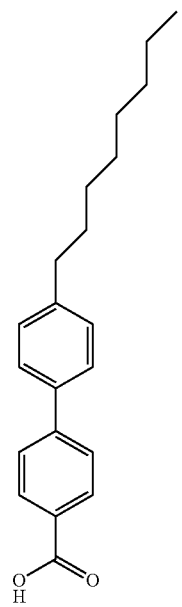

Formula II or a pharmaceutically acceptable salt, wherein said pharmaceutical composition further comprising a pharmaceutically acceptable carrier, thereby treating said disease in said subject.

6. The method of claim 5, wherein said liver disease is associated with diabetes.

7. The method of claim 6, wherein said diabetes is type I or type II diabetes, or gestational diabetes.

8. The method of claim 5, wherein said pharmaceutical composition comprises both of said compound set forth in Formula I and said compound set forth in Formula II.

9. The method of claim 5, wherein said liver disease is fatty liver disease (FLD), liver fibrosis, or hepatic steatosis.

10. The method of claim 5, wherein said liver disease is non-alcoholic FLD (NAFLD), alcohol associated FLD, or non-alcoholic steatohepatitis (NASH).

11. A method of treating a kidney disease associated with reduced vitamin A levels in the kidney in a subject in need thereof, the method comprising administering to said subject a pharmaceutical composition comprising an agonist of retinoic acid receptor-beta (RARβ), wherein said agonist is a compound set forth in Formula I, Formula I a compound set forth in Formula II, Formula II

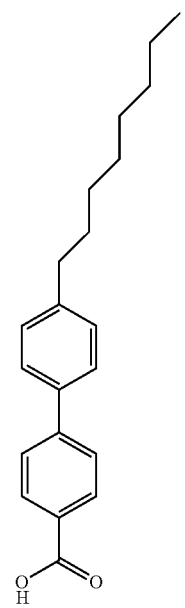

or a pharmaceutically acceptable salt, wherein said pharmaceutical composition further comprising a pharmaceutically acceptable carrier, thereby treating said disease in said subject.

12. The method of claim 11, wherein said kidney disease is associated with diabetes.

13. The method of claim 12, wherein said diabetes is type I or type II diabetes, or gestational diabetes.

14. The method of claim 11, wherein said pharmaceutical composition comprises both of said compound set forth in Formula I and said compound set forth in Formula II.

15. The method of claim 11, wherein said kidney disease is kidney fibrosis.

16. The method of claim 11, wherein said kidney disease is a chronic kidney disease.

* * * * *